(12) United States Patent
Connor et al.

(10) Patent No.: US 8,162,966 B2
(45) Date of Patent: Apr. 24, 2012

(54) SURGICAL DEVICES INCORPORATING LIQUID JET ASSISTED TISSUE MANIPULATION AND METHODS FOR THEIR USE

(75) Inventors: Brian G. Connor, Newfields, NH (US); Joseph P. Sylvester, Jr., New Hampton, NH (US); Paul T. Modoono, Chelmsford, MA (US); Kevin P. Staid, Lowell, MA (US); David M. Reed, New Canaan, CT (US)

(73) Assignee: Hydrocision, Inc., North Billerica, MA (US)

( * ) Notice: Subject to any disclaimer, the term of this patent is extended or adjusted under 35 U.S.C. 154(b) by 1228 days.

(21) Appl. No.: 10/695,632

(22) Filed: Oct. 27, 2003

(65) Prior Publication Data
US 2004/0243157 A1 Dec. 2, 2004

Related U.S. Application Data

(60) Provisional application No. 60/421,219, filed on Oct. 25, 2002, provisional application No. 60/444,344, filed on Jan. 31, 2003, provisional application No. 60/488,024, filed on Jul. 17, 2003.

(51) Int. Cl.
*A61B 17/32* (2006.01)
(52) U.S. Cl. .................. 606/170; 606/160
(58) Field of Classification Search .......... 606/167, 606/131, 166, 159, 170, 160; 604/22, 70; 451/36
See application file for complete search history.

(56) References Cited

U.S. PATENT DOCUMENTS

| | | | |
|---|---|---|---|
| 1,889,425 A | 11/1932 | Sorensen |
| 1,902,418 A | 3/1933 | Pilgrim |
| 2,429,356 A | 10/1947 | Hicks |
| 2,937,444 A | 5/1960 | Kern |
| 3,128,079 A | 4/1964 | De Groff |
| 3,210,848 A | 10/1965 | Bizzigotti |
| 3,565,062 A | 2/1971 | Kuris |
| 3,578,872 A | 5/1971 | McBurnie |
| 3,590,813 A | 7/1971 | Roszyk |

(Continued)

FOREIGN PATENT DOCUMENTS
DE 29 33 266 A1 5/1981
(Continued)

OTHER PUBLICATIONS
Othopedic Sourcebook "Instruments for Surgeons" KMedic 1999.
(Continued)

*Primary Examiner* — Gary Jackson
*Assistant Examiner* — Katherine Dowe
(74) *Attorney, Agent, or Firm* — McCarter & English, LLP

(57) ABSTRACT

Surgical instruments are disclosed that utilize high-pressure liquid jets to perform a variety of useful functions. In certain embodiments, surgical instruments are described incorporating one or more liquid jets utilized to contact tissue excised by a non-liquid jet tissue-cutting component of the surgical instrument. In certain embodiments, a liquid jet of a surgical instrument can be utilized for the purpose of excising tissue of a patient immobilized and/or manipulated by the surgical instrument. Also described are surgical devices of the type characterized by curettes, rongeurs, bone punches, bone cutting forceps, morcellators, surgical micrograspers, with functionality and performance supplemented by the integration of a liquid jet. Also disclosed are methods of using certain liquid jet-containing surgical instruments for performing surgical procedures, for example surgical procedures on the spinal column of a patient.

30 Claims, 11 Drawing Sheets

U.S. PATENT DOCUMENTS

| | | |
|---|---|---|
| 3,731,384 A | 5/1973 | Brooks et al. |
| 3,731,385 A | 5/1973 | Farber et al. |
| 3,818,913 A | 6/1974 | Wallach |
| 3,835,858 A | 9/1974 | Hagen |
| 3,844,272 A | 10/1974 | Banko |
| 3,906,954 A | 9/1975 | Baehr et al. |
| 3,930,505 A | 1/1976 | Wallach |
| 3,937,222 A | 2/1976 | Banko |
| 3,976,077 A | 8/1976 | Kerfoot, Jr. |
| 4,024,866 A | 5/1977 | Wallach |
| 4,061,146 A | 12/1977 | Baehr et al. |
| 4,111,490 A | 9/1978 | Liesveld |
| 4,137,804 A | 2/1979 | Gerber et al. |
| 4,203,444 A | 5/1980 | Bonnell et al. |
| 4,229,139 A | 10/1980 | Marantette et al. |
| 4,235,595 A | 11/1980 | Arnegger |
| 4,245,624 A | 1/1981 | Komiya |
| 4,282,867 A | 8/1981 | Du Toit |
| 4,294,251 A | 10/1981 | Greenwald et al. |
| 4,320,761 A | 3/1982 | Haddad |
| 4,368,734 A | 1/1983 | Banko |
| 4,435,902 A | 3/1984 | Mercer et al. |
| 4,445,509 A | 5/1984 | Auth |
| 4,499,899 A | 2/1985 | Lyons, III |
| 4,512,344 A | 4/1985 | Barber |
| 4,517,977 A | 5/1985 | Frost |
| 4,522,206 A | 6/1985 | Whipple et al. |
| 4,545,374 A | 10/1985 | Jacobson |
| 4,560,373 A | 12/1985 | Sugino et al. |
| 4,583,531 A | 4/1986 | Mattchen |
| 4,589,412 A | 5/1986 | Kensey |
| 4,631,052 A | 12/1986 | Kensey |
| 4,637,551 A | 1/1987 | Seeger, Jr. et al. |
| 4,690,140 A | 9/1987 | Mecca |
| 4,690,672 A | 9/1987 | Veltrup |
| 4,694,828 A | 9/1987 | Eichenbaum |
| 4,705,038 A | 11/1987 | Sjostrom et al. |
| 4,715,848 A | 12/1987 | Beroza |
| 4,729,763 A | 3/1988 | Henrie |
| 4,735,604 A | 4/1988 | Watmough et al. |
| 4,735,620 A | 4/1988 | Ruiz |
| 4,747,821 A | 5/1988 | Kensey et al. |
| 4,749,376 A | 6/1988 | Kensey et al. |
| 4,770,174 A | 9/1988 | Luckman et al. |
| 4,790,813 A | 12/1988 | Kensey |
| 4,798,339 A | 1/1989 | Sugino et al. |
| 4,815,462 A | 3/1989 | Clark |
| 4,827,615 A | 5/1989 | Graham |
| 4,827,679 A | 5/1989 | Earle, III |
| 4,839,492 A | 6/1989 | Bouchier et al. |
| 4,842,578 A | 6/1989 | Johnson et al. |
| 4,898,574 A | 2/1990 | Uchiyama et al. |
| 4,913,698 A | 4/1990 | Ito et al. |
| 4,935,006 A | 6/1990 | Hasson |
| 4,937,985 A | 7/1990 | Boers et al. |
| 4,986,807 A | 1/1991 | Farr |
| 5,002,546 A | 3/1991 | Romano |
| 5,018,670 A | 5/1991 | Chalmers |
| 5,027,792 A | 7/1991 | Meyer |
| 5,037,431 A | 8/1991 | Summers et al. |
| 5,042,984 A | 8/1991 | Kensey et al. |
| 5,052,624 A | 10/1991 | Boers et al. |
| 5,057,098 A | 10/1991 | Zelman |
| 5,074,862 A | 12/1991 | Rausis |
| 5,097,849 A | 3/1992 | Kensey et al. |
| 5,111,652 A | 5/1992 | Andre |
| 5,112,299 A | 5/1992 | Pascaloff |
| 5,114,399 A | 5/1992 | Kovalcheck |
| 5,125,582 A | 6/1992 | Surjaatmadja et al. |
| 5,135,482 A | 8/1992 | Neracher |
| 5,135,484 A | 8/1992 | Wright |
| 5,162,016 A | 11/1992 | Malloy |
| 5,186,714 A | 2/1993 | Boudreault et al. |
| 5,195,958 A | 3/1993 | Phillips |
| 5,195,959 A | 3/1993 | Smith |
| 5,217,465 A | 6/1993 | Steppe |
| 5,230,704 A | 7/1993 | Moberg et al. |
| 5,205,779 A | 8/1993 | O'Brien et al. |
| 5,242,449 A | 9/1993 | Zaleski |
| 5,250,065 A | 10/1993 | Clement et al. |
| 5,254,117 A | 10/1993 | Rigby et al. |
| 5,255,017 A | 10/1993 | Lam |
| 5,259,842 A | 11/1993 | Plechinger et al. |
| 5,275,607 A | 1/1994 | Lo et al. |
| 5,286,253 A | 2/1994 | Fucci |
| RE34,556 E | 3/1994 | Sjostrom et al. |
| 5,300,022 A | 4/1994 | Klapper et al. |
| 5,312,400 A | 5/1994 | Bales et al. |
| 5,314,375 A | 5/1994 | O'Brien et al. |
| 5,314,406 A | 5/1994 | Arias et al. |
| 5,318,518 A * | 6/1994 | Plechinger et al. ............ 604/43 |
| 5,320,599 A | 6/1994 | Griep et al. |
| 5,322,504 A | 6/1994 | Doherty et al. |
| 5,339,799 A | 8/1994 | Kami et al. |
| 5,348,555 A | 9/1994 | Zinnanti |
| 5,350,390 A | 9/1994 | Sher |
| 5,364,395 A | 11/1994 | West, Jr. |
| 5,370,609 A | 12/1994 | Drasler et al. |
| 5,383,876 A | 1/1995 | Nardella |
| 5,395,312 A | 3/1995 | Desai |
| 5,395,315 A | 3/1995 | Griep |
| 5,395,369 A | 3/1995 | McBrayer et al. |
| 5,409,376 A | 4/1995 | Murphy |
| 5,429,596 A | 7/1995 | Arias et al. |
| 5,437,662 A | 8/1995 | Nardella |
| 5,441,482 A | 8/1995 | Clague et al. |
| 5,441,499 A | 8/1995 | Fritzsch |
| 5,449,357 A | 9/1995 | Zinnanti |
| 5,449,369 A | 9/1995 | Imran |
| 5,451,223 A | 9/1995 | Ben-Simhon |
| 5,453,088 A | 9/1995 | Boudewijn et al. |
| 5,454,827 A | 10/1995 | Aust et al. |
| 5,468,028 A | 11/1995 | Olson |
| 5,476,450 A | 12/1995 | Ruggio |
| 5,484,441 A | 1/1996 | Koros et al. |
| 5,496,267 A * | 3/1996 | Drasler et al. .................. 604/22 |
| 5,505,729 A | 4/1996 | Rau |
| 5,512,044 A | 4/1996 | Duer |
| 5,520,685 A | 5/1996 | Wojciechowicz |
| 5,524,821 A | 6/1996 | Yie et al. |
| 5,527,330 A | 6/1996 | Tovey |
| 5,527,331 A | 6/1996 | Kresch et al. |
| 5,527,332 A | 6/1996 | Clement |
| 5,549,606 A | 8/1996 | McBrayer et al. |
| 5,551,448 A | 9/1996 | Matula et al. |
| 5,554,112 A | 9/1996 | Walbrink et al. |
| 5,556,406 A | 9/1996 | Gordon et al. |
| 5,562,640 A | 10/1996 | McCabe et al. |
| 5,562,692 A | 10/1996 | Bair |
| 5,569,258 A | 10/1996 | Gambale |
| 5,584,855 A | 12/1996 | Onik |
| 5,591,184 A | 1/1997 | McDonnell et al. |
| 5,607,391 A | 3/1997 | Klinger et al. |
| 5,609,573 A | 3/1997 | Sandock |
| 5,618,293 A | 4/1997 | Sample et al. |
| 5,620,414 A | 4/1997 | Campbell, Jr. |
| 5,643,299 A | 7/1997 | Bair |
| 5,653,713 A | 8/1997 | Michelson |
| 5,658,249 A | 8/1997 | Beland et al. |
| 5,662,680 A | 9/1997 | Desai |
| 5,667,480 A | 9/1997 | Knight et al. |
| 5,672,945 A | 9/1997 | Krause |
| 5,674,226 A | 10/1997 | Doherty et al. |
| 5,683,366 A | 11/1997 | Eggers et al. |
| 5,685,840 A | 11/1997 | Schechter et al. |
| 5,685,877 A | 11/1997 | Pagedas et al. |
| 5,688,269 A | 11/1997 | Newton et al. |
| 5,697,281 A | 12/1997 | Eggers et al. |
| 5,697,536 A | 12/1997 | Eggers et al. |
| 5,697,882 A | 12/1997 | Eggers et al. |
| 5,702,387 A | 12/1997 | Arts et al. |
| 5,709,697 A | 1/1998 | Ratcliff et al. |
| 5,713,849 A | 2/1998 | Bosma et al. |
| 5,713,851 A | 2/1998 | Boudewijn et al. |
| 5,713,878 A | 2/1998 | Moutafis et al. |
| 5,730,742 A | 3/1998 | Wojciechowicz |
| 5,735,815 A | 4/1998 | Bair |

| | | | | | | |
|---|---|---|---|---|---|---|
| 5,749,885 | A | 5/1998 | Sjostrom et al. | 2005/0159765 A1 | 7/2005 | Moutafis et al. |
| 5,766,167 | A | 6/1998 | Eggers et al. | 2005/0267443 A1 | 12/2005 | Staid et al. |
| 5,766,177 | A | 6/1998 | Lucas-Dean et al. | 2005/0283150 A1 | 12/2005 | Moutafis et al. |
| 5,779,713 | A | 7/1998 | Turjanski et al. | 2006/0229550 A1 | 10/2006 | Staid et al. |
| 5,782,795 | A | 7/1998 | Bays | 2006/0264808 A1 | 11/2006 | Staid et al. |
| 5,782,829 | A | 7/1998 | Swiantek et al. | | | |
| 5,785,675 | A | 7/1998 | Drasler et al. | | | |

FOREIGN PATENT DOCUMENTS

| | | |
|---|---|---|
| 5,788,667 A | 8/1998 | Stoller |
| 5,792,139 A | 8/1998 | Chambers et al. |
| 5,792,167 A | 8/1998 | Kablik et al. |
| 5,797,907 A | 8/1998 | Clement |
| 5,803,733 A | 9/1998 | Trott et al. |
| 5,810,809 A | 9/1998 | Rydell |
| 5,827,323 A | 10/1998 | Klieman et al. |
| 5,830,214 A | 11/1998 | Flom et al. |
| 5,843,017 A | 12/1998 | Yoon |
| 5,843,021 A | 12/1998 | Edwards et al. |
| 5,849,023 A | 12/1998 | Mericle |
| 5,851,214 A | 12/1998 | Larsen et al. |
| 5,853,384 A | 12/1998 | Bair |
| 5,861,002 A | 1/1999 | Desai |
| 5,868,742 A | 2/1999 | Manes et al. |
| 5,868,785 A | 2/1999 | Tal et al. |
| 5,871,462 A | 2/1999 | Yoder et al. |
| 5,879,358 A | 3/1999 | Semm |
| 5,899,915 A | 5/1999 | Saadat |
| 5,904,681 A | 5/1999 | West, Jr. |
| 5,913,867 A | 6/1999 | Dion |
| 5,927,976 A | 7/1999 | Wu |
| 5,941,876 A | 8/1999 | Nardella et al. |
| 5,941,893 A | 8/1999 | Saadat |
| 5,944,686 A * | 8/1999 | Patterson et al. ............... 604/22 |
| 5,947,988 A | 9/1999 | Smith |
| 5,961,531 A | 10/1999 | Weber et al. |
| 6,007,533 A | 12/1999 | Casscells et al. |
| 6,013,076 A | 1/2000 | Goble et al. |
| 6,017,354 A | 1/2000 | Culp et al. |
| 6,036,698 A | 3/2000 | Fawzi et al. |
| 6,045,564 A | 4/2000 | Walen |
| 6,053,923 A | 4/2000 | Veca et al. |
| 6,066,150 A | 5/2000 | Gonon |
| 6,083,189 A | 7/2000 | Gonon et al. |
| 6,096,001 A | 8/2000 | Drasler et al. |
| 6,099,514 A | 8/2000 | Sharkey et al. |
| 6,110,169 A | 8/2000 | Mueller et al. |
| 6,129,740 A | 10/2000 | Michelson |
| 6,135,977 A | 10/2000 | Drasler et al. |
| 6,142,997 A | 11/2000 | Michelson |
| 6,149,622 A | 11/2000 | Marie |
| 6,200,320 B1 | 3/2001 | Michelson |
| 6,206,898 B1 | 3/2001 | Honeycutt et al. |
| 6,214,010 B1 | 4/2001 | Farley et al. |
| 6,216,573 B1 | 4/2001 | Moutafis et al. |
| 6,280,302 B1 | 8/2001 | Hashish et al. |
| 6,322,533 B1 | 11/2001 | Gonon |
| 6,375,635 B1 | 4/2002 | Moutafis et al. |
| 6,402,715 B2 | 6/2002 | Manhes |
| 6,419,654 B1 | 7/2002 | Kadan |
| 6,423,028 B1 | 7/2002 | Gonon |
| 6,451,017 B1 | 9/2002 | Moutafis et al. |
| 6,464,567 B2 | 10/2002 | Hashish et al. |
| 6,491,660 B2 | 12/2002 | Guo et al. |
| 6,508,823 B1 | 1/2003 | Gonon |
| 6,511,493 B1 | 1/2003 | Moutafis et al. |
| 6,544,220 B2 | 4/2003 | Shuman et al. |
| 6,669,710 B2 | 12/2003 | Moutafis et al. |
| 6,899,712 B2 | 5/2005 | Moutafis et al. |
| 6,923,792 B2 | 8/2005 | Staid et al. |
| 6,960,182 B2 | 11/2005 | Moutafis et al. |
| 7,122,017 B2 | 10/2006 | Moutafis et al. |
| 2001/0002562 A1 | 6/2001 | Moutafis et al. |
| 2002/0176788 A1 | 11/2002 | Moutafis et al. |
| 2003/0055404 A1 | 3/2003 | Moutafis |
| 2003/0083681 A1 | 5/2003 | Moutafis et al. |
| 2003/0125660 A1 | 7/2003 | Moutafis et al. |
| 2004/0228736 A1 | 11/2004 | Moutafis et al. |
| 2004/0230211 A1 | 11/2004 | Moutafis et al. |
| 2004/0234380 A1 | 11/2004 | Moutafis et al. |
| 2004/0243157 A1 | 12/2004 | Connor et al. |

| | | |
|---|---|---|
| DE | 3 320 076 A1 | 12/1984 |
| DE | 3 421 390 A1 | 12/1985 |
| DE | 40 18 736 A1 | 1/1992 |
| DE | 19 734 890 C1 | 7/1999 |
| EP | 0 175 096 | 3/1986 |
| EP | 0 253 478 B1 | 1/1988 |
| EP | 0 258 901 A2 | 3/1988 |
| EP | 0 280 972 A1 | 9/1988 |
| EP | 0 335 861 | 10/1989 |
| EP | 0 367 855 A1 | 5/1990 |
| EP | 0367855 A | 5/1990 |
| EP | 0 411 170 A1 | 2/1991 |
| EP | 0 442 579 A1 | 8/1991 |
| EP | 0 470 781 A1 | 2/1992 |
| EP | 0 485 133 A1 | 5/1992 |
| EP | 0 489 496 A1 | 6/1992 |
| EP | 0 551 920 B1 | 7/1993 |
| EP | 0 555 549 A1 | 8/1993 |
| EP | 0 620 016 A1 | 10/1994 |
| EP | 0 636 345 A1 | 2/1995 |
| EP | 0 637 453 A1 | 2/1995 |
| EP | 0 693 295 A1 | 1/1996 |
| EP | 0 737 450 A1 | 10/1996 |
| EP | 0 771 176 B1 | 5/1997 |
| EP | 0 806 213 A1 | 11/1997 |
| EP | 1 025 807 A2 | 8/2000 |
| FR | 2 779 934 | 12/1999 |
| FR | 2 779 935 | 12/1999 |
| JE | HEI 9-122133 | 5/1997 |
| JP | HEI5-193143 | 8/1993 |
| JP | HEI6-240488 | 8/1994 |
| WO | WO 90/05493 | 5/1990 |
| WO | WO 94/10917 | 5/1994 |
| WO | WO 94/28807 | 12/1994 |
| WO | WO 96/24299 | 8/1996 |
| WO | WO 96/39914 | 12/1996 |
| WO | WO 96/39954 | 12/1996 |
| WO | WO 96/40476 | 12/1996 |
| WO | WO 97/00647 | 1/1997 |
| WO | WO 97/03713 | 2/1997 |
| WO | WO 97/24074 | 10/1997 |
| WO | WO 97/48345 | 12/1997 |
| WO | WO 97/49441 | 12/1997 |
| WO | WO 99/33510 | 7/1999 |
| WO | WO 99/65407 | 12/1999 |
| WO | WO 99/65408 | 12/1999 |
| WO | WO 99/66848 | 12/1999 |
| WO | WO 00/69348 | 11/2000 |
| WO | WO 0069348 A1 | 11/2000 |
| WO | WO 01/22890 A1 | 4/2001 |
| WO | WO 01/50965 | 7/2001 |
| WO | WO 01/50966 | 7/2001 |
| WO | WO 02/095234 A1 | 11/2002 |
| WO | WO 03/013645 A1 | 2/2003 |
| WO | WO 03/024340 A2 | 3/2003 |
| WO | WO 03/045259 | 6/2003 |
| WO | WO 2004/037095 A2 | 5/2004 |
| WO | WO 2004/069064 A2 | 8/2004 |
| WO | WO 2006/066160 | 6/2006 |

OTHER PUBLICATIONS

The Anspach Effort Inc. "Black Max" 2 pgs printed from www.anspach.com/blackmax.php, Oct. 28, 2003.
The Anspach Effort Inc. "Micro Max" 2 pgs printed from www.anspach.com/micromax.php, Oct. 28, 2003.
The Anspach Effort Inc. "Micro Max plus" 2 pgs printed from www.anspach.com/micromax_plus.php, Oct. 28, 2003.
The Anspach Effort Inc. "E Max" 3 pgs printed from www.anspach.com/emax.php, Oct. 28, 2003.
The Anspach Effort Inc. "Black Max Attachments Accessories" 8 pgs printed from www.anspach.com/blackmaxattach.php, Oct. 28, 2003.

The Anspach Effort Inc. "Universal Attachments Accessories" 3 pgs printed from www.anspach.com/universal_attachments.php, Oct. 28, 2003.

Aeikens, B. "Cracking of Ureter Calculi by High Speed Water Jet Pulses," 8th International Symposium on Jet Cutting Technology, Paper 15, pp. 157/166, Sep. 9, 2011, 1986.

Baer et al. "Jet/Cutting / an Alternative to the Ultrasonic Aspirator?" Chirurg, 61:735, 1990 and Reply to commentary.

Baer et al., "Hepatic Surgery Facilitated by a New Jet Dissector," HPB Surgery, vol. 4, pp. 137/146, 1991.

Baer et al., "New water/jet dissector: initial experience in hepatic surgery," Br. J. Surg., vol. 78, pp. 502/503, Apr. 1991.

Baer et al., "Subtotal hepatectomy: a new procedure based on the inferior right hepatic vein," Br. J. Surg., vol. 78, pp. 1221/1222, Oct. 1991.

Baer et al., "Water/jet dissection in hepatic surgery," Minimally Invasive Therapy, vol. 1, pp. 169/172, 1992.

Balje, O.E., *Turbomachines a Guide to Design, Selection, and Theory*, John Wiley & Sons Publisher, Chap. 5, Sect. 3, pp. 252/259, 1981.

Beard, J. "Water jet puts surgeons at the cutting edge," New Scientist, Jul. 23, 1994.

Bücker et al., "Comparative in Vitro Study of Two Percutaneous Hydrodynamic Thrombectomy Systems," Journal of Vascular and Interventional Radiology, vol. 7, No. 3, pp. 445/449, May/Jun. 1996.

Douek et al., "Functional Properties of a Prototype Rheolytic Catheter for Percutaneous Thrombectomy In Vitro Investigations," Investigative Radiology, vol. 29, No. 5, pp. 547/552, 1994.

Drasler et al., "A Rheolytic System for Percutaneous Coronary and Peripheral Plaque Removal," Angiology/The Journal of Vascular Diseases, vol. 42, No. 2, pp. 90/98, Feb. 1991.

Drasler et al., "Rheolytic Catheter for Percutaneous Removal of Thrombus," Radiology, vol. 182, pp. 263/267, Jan. 1992.

Field, J.E. "The physics of liquid impact, shock wave interactions with cavities, and the implications to shock wave lithotripsy," Phys. Med. Biol., vol. 36, No. 11, pp. 1475/1484, 1991.

Giraud et al., "Bone cutting," Clin. Phys. Physiol. Meas., vol. 12, No. 1, pp. 1/19, 1991.

Hata et al., "Liver Resection in Children, Using a Water/Jet," Journal of Pediatric Surgery, vol. 29, No. 5, pp. 648/650, May 1994.

Izumi et al., "Hepatic Resection Using a Water Jet Dissector," Surgery Today Jpn. J. Surg., vol. 23, pp. 31/35, 1993.

Jessen et al., "Endoscopic Jet Cutting of Human Gallstones," 7th Internal Symposium on Jet Cutting Technology, Paper D4, pp. 211/220, Jun. 26/28, 1984.

Jessen et al., K. "Endoscopic Jet/Cutting a New Method for Stone Destruction in the Common Bile Duct," 6th Internal Symposium on Jet Cutting Technology, Paper B1, pp. 39/52, Apr. 6/8, 1982.

Kobayashi et al., "Experimental Study of Water Jet Angioplasty," Vascular Surgery—International Conference, Oct. 1993, vol. 2, pp. 626/631.

Müller-Hülsbeck et al., S. "Rheolytic Thrombectomy of an Acutely Thrombosed Transjugular Intrahepatic Portosystemic Stent Shunt," CardioVasc. Intervent. Radiol., vol. 19, pp. 294/297, 1996.

Overbosch et al., E.H. "Occluded Hemodialysis Shunts: Dutch Multicenter Experience with the Hydrolyser Catheter," Radiology, vol. 201, No. 2, pp. 485/488, 1996.

Papachristou et al., "Resection of the liver with a water jet," Br. J. Surg., vol. 69, pp. 93/94 (1982).

Persson et al., "Transection of the Liver with a Water Jet," Surgery, Gynecology & Obstetrics, vol. 168, pp. 267/268, Mar. 1989.

Reekers et al., J.A. "Catheter for Percutaneous Thrombectomy: First Clinical Experience," Radiology, vol. 188, No. 3, pp. 871/874, 1993.

Schob et al., "The Multimodal Water Jet Dissector / a Technology for Laparoscopic Liver Surgery," End. Surg., vol. 2, pp. 311/314, 1994.

Schob et al., O.M. "Experimental laparoscopic liver resection with a multimodal water jet dissector," British Journal of Surgery, vol. 82, pp. 392/393, 1995.

Shimi, S.M. "Dissection techniques in laparoscopic surgery: a review," J.R. Coll. Surg. Edinb., vol. 40, pp. 249/259, Aug. 1995.

Spence, R.K. "Emerging Trends in Surgical Blood Transfusion," Seminars in Hematology, vol. 34, No. 3, Suppl 2, pp. 48/53, Jul. 1997.

Summers, D.A. and J. Viebrock, "The Impact of Waterjets on Human Flesh," 9th International Symposium on Jet Cutting Technology, Paper H4, pp. 423/433, Oct. 4/6, 1988.

Terzis et al., A.J.A. "A New System for Cutting Brain Tissue Preserving Vessels: water jet cutting," British Journal of Neurosurgery, vol. 3, pp. 361/366, 1989.

Truchot et al., P. "Development of a Cryogenic Waterjet Technique for Biomaterial Processing Applications," 6th American Water Jet Conference, Paper 35, pp. 473/480. Aug. 24/27, 1991.

Uchino, J., et al., "Surgical Cutting of the Liver by Water Jet," 9th International Symposium on Jet Cutting Technology, Poster 1, pp. 629/639, Oct. 4/6, 1988.

Van Ommen et al., V.G. "Removal of Thrombus from Aortocoronary Bypass Grafts and Coronary Arteries Using the 6Fr Hydrolyser," The American Journal of Cardiology, vol. 79, pp. 1012/1016, Apr. 1997.

Vijay, M.M. "A Critical Examination of the Use of Water Jets for Medical Applications," 5th American Water Jet Conference, Paper/Communication 42, pp. 425/448, Aug. 29/31, 1989.

Water Jet Dissector, Hepatotom® Supersonic Microjet Dissector brochure, Medical Exports AG.

Wilson et al.., The Design of High/Efficiency Turbomachinery and Gas Turbines, Prentice Hall Publisher, 2nd edition, p. 31, 1998.

Zhong et al., P. "Propagation of shock waves in elastic solids caused by cavitation microjet impact. II: Application in extracorporeal shock wave lithotripsy," J. Acoust. Soc. Am., vol. 94, No. 1, pp. 29/36, Jul. 1993.

International Search Report published May 6, 2004 for copending International Application No. PCT-US2003/034174—published as WO 04/037095 A3.

Office Action issued by the Japanese Patent Office in Japanese Application No. 2005-501705, dated Sep. 11, 2009.

Communication pursuant to Article 94(3) EPC by the European Patent Office in European Application No. 04 707 378.8-2310, dated Oct. 1, 2009.

Office Action issued by the Japanese Patent Office in Japanese Application No. 2006-503244, dated Sep. 16, 2009.

Office Action issued by the Japanese Patent Office in Japanese Application No. 2006-503244, dated Oct. 2010.

Examination Report issued by the Australian Patent Office in Australian Application No. 2004209990, dated Feb. 16, 2009.

International Search Report issued in International Application No. PCT/US2004/002893, dated Nov. 8, 2004.

International Preliminary Report on Patentability issued in International Application No. PCT/US2004/0002893, dated Aug. 5, 2005.

International Search Report issued in International Application No. PCT/US2003/034174, dated Jul. 16, 2004.

Examination Report issued in Australian Application No. 2003301525, dated Sep. 15, 2008.

Communication pursuant to Article 94(3) EPC by the European Patent Office in European Application No. 03809652.5, dated Nov. 20, 2008.

Written Opinion issued in International Application No. PCT/US2004/002893, dated Jul. 31, 2005.

Examination Report issued by the Canadian Patent Office in Canadian Application No. 2,554,930, dated Jul. 5, 2011.

European Office Action for Application No. 03809652.5, dated Nov. 20, 2008.

* cited by examiner

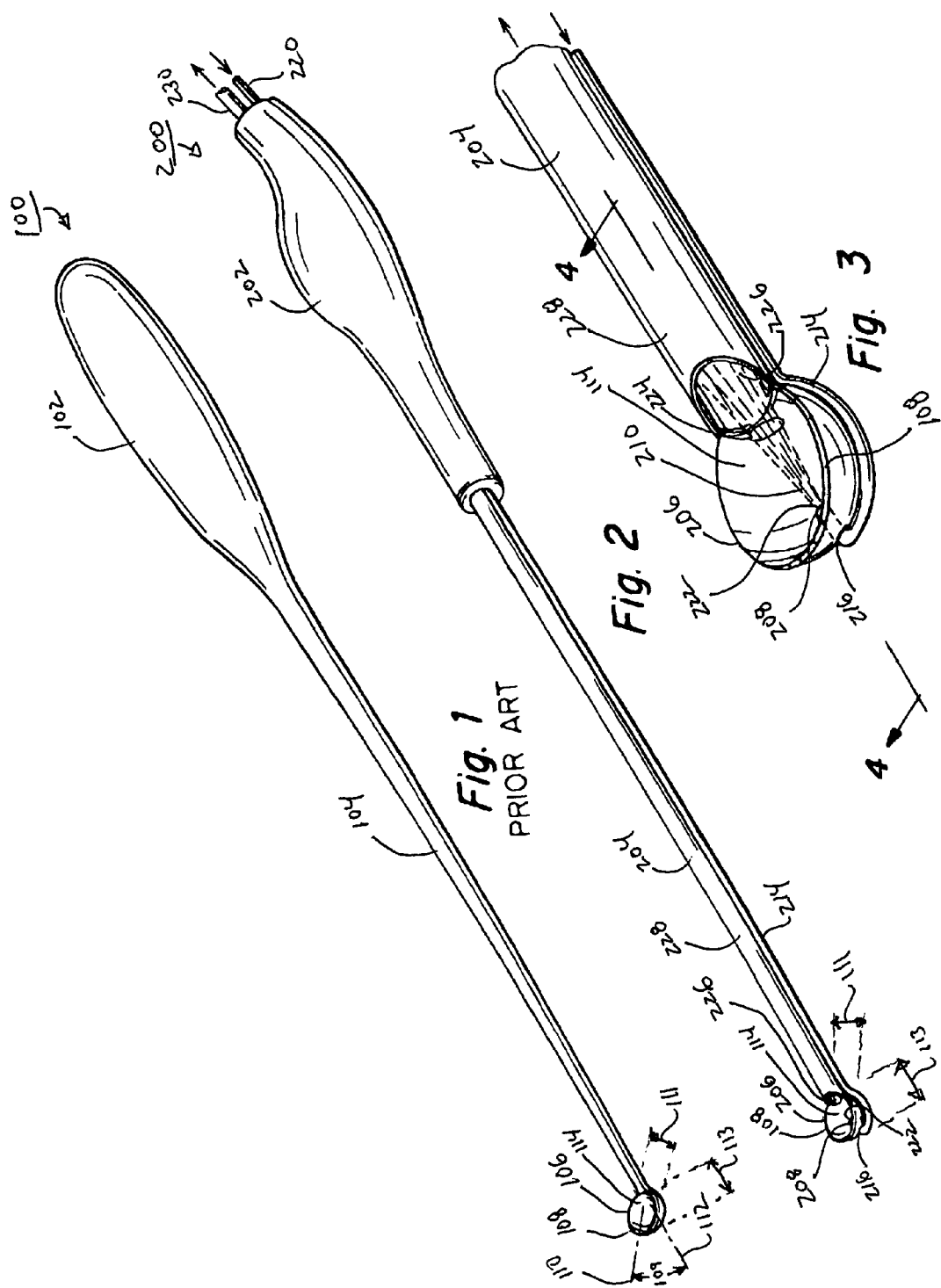

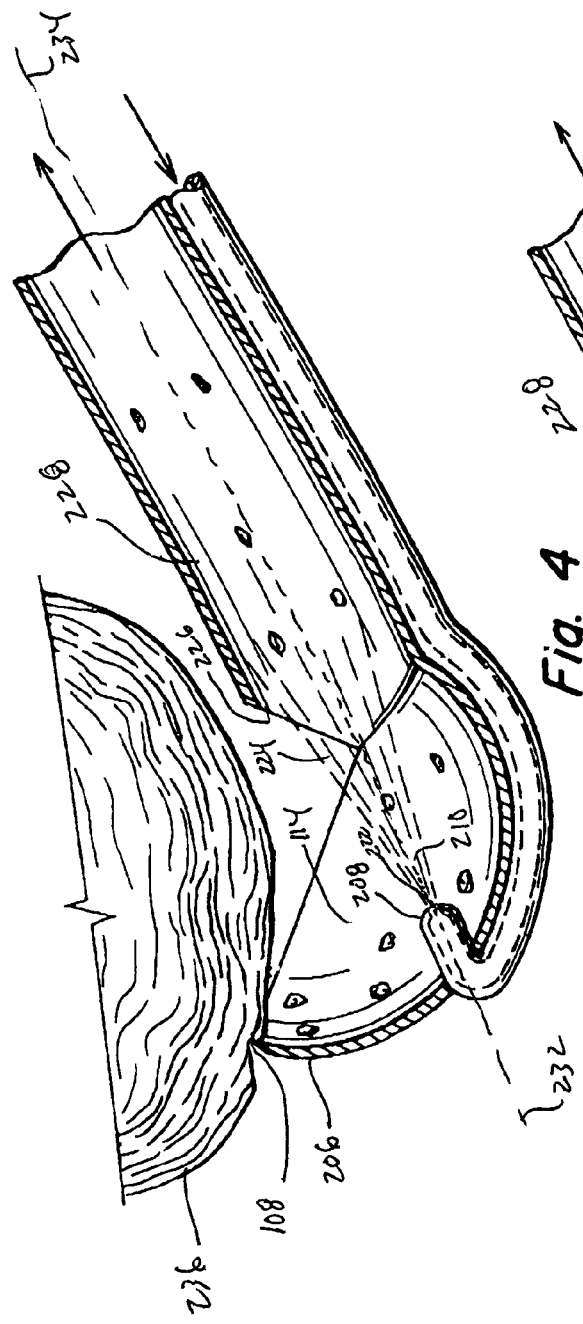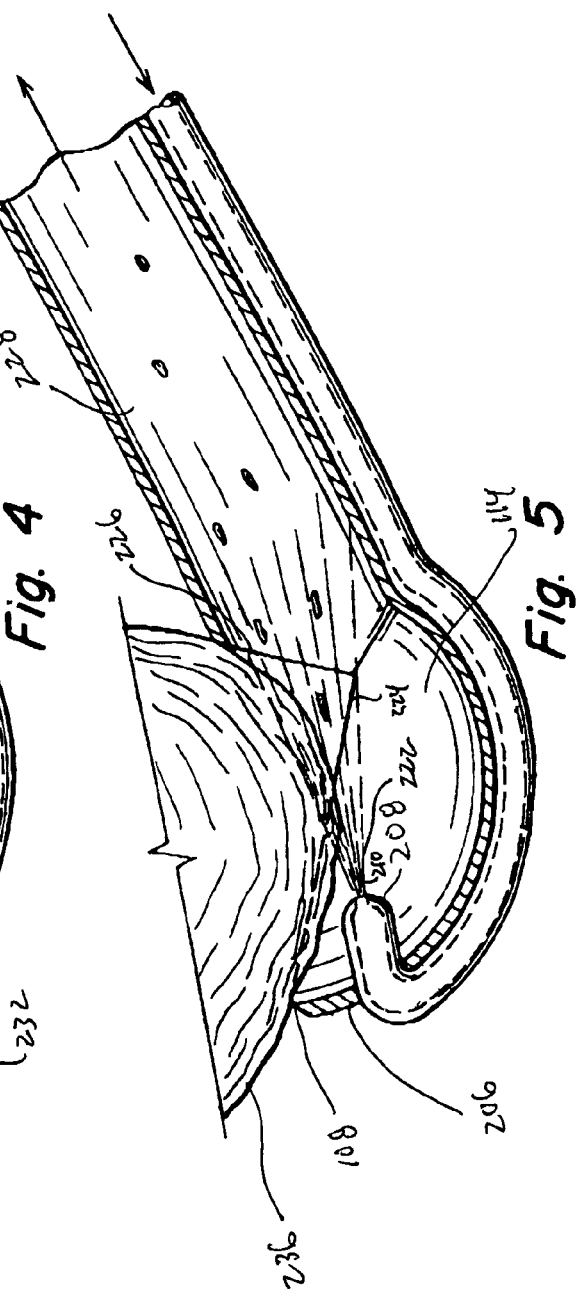

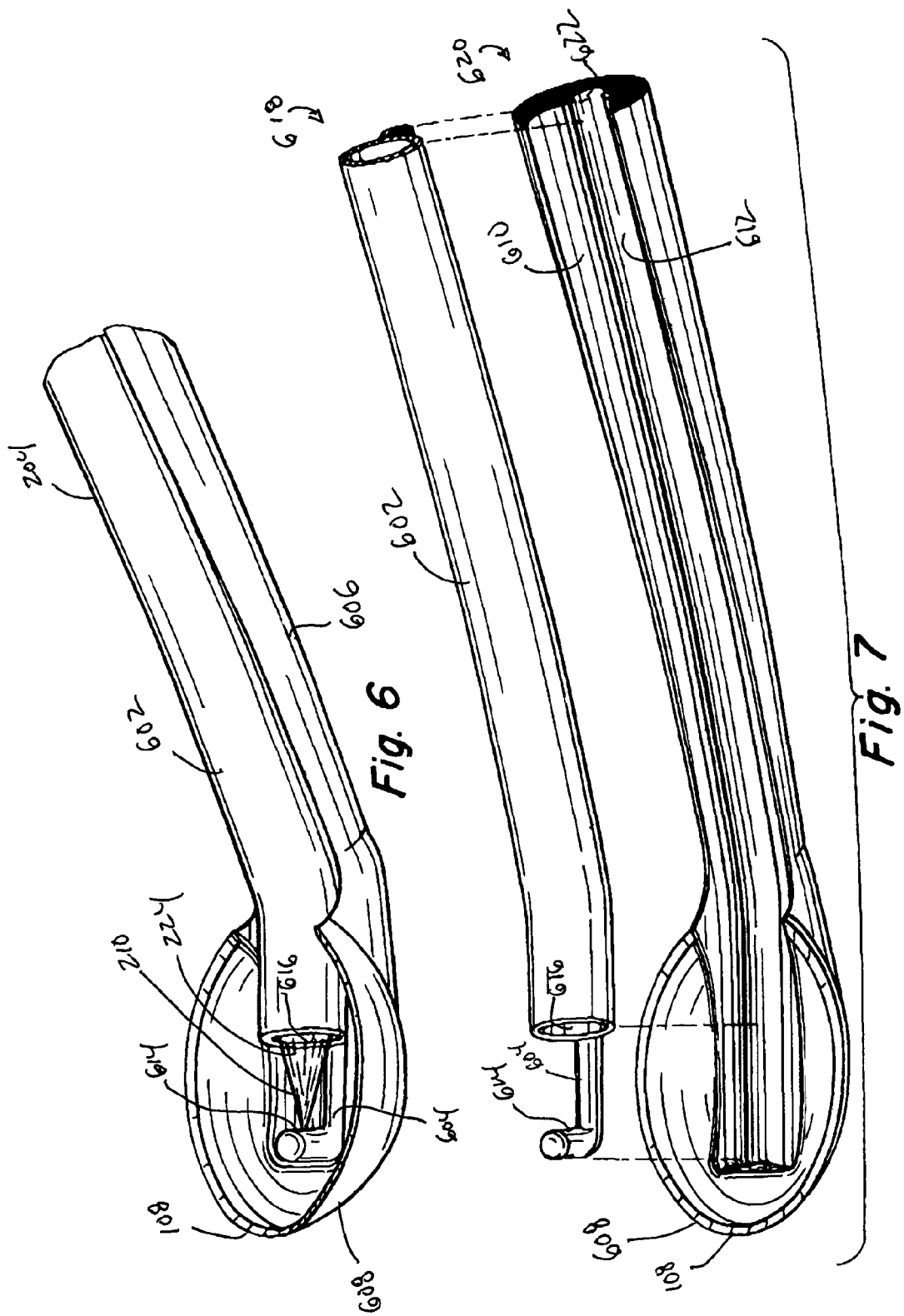

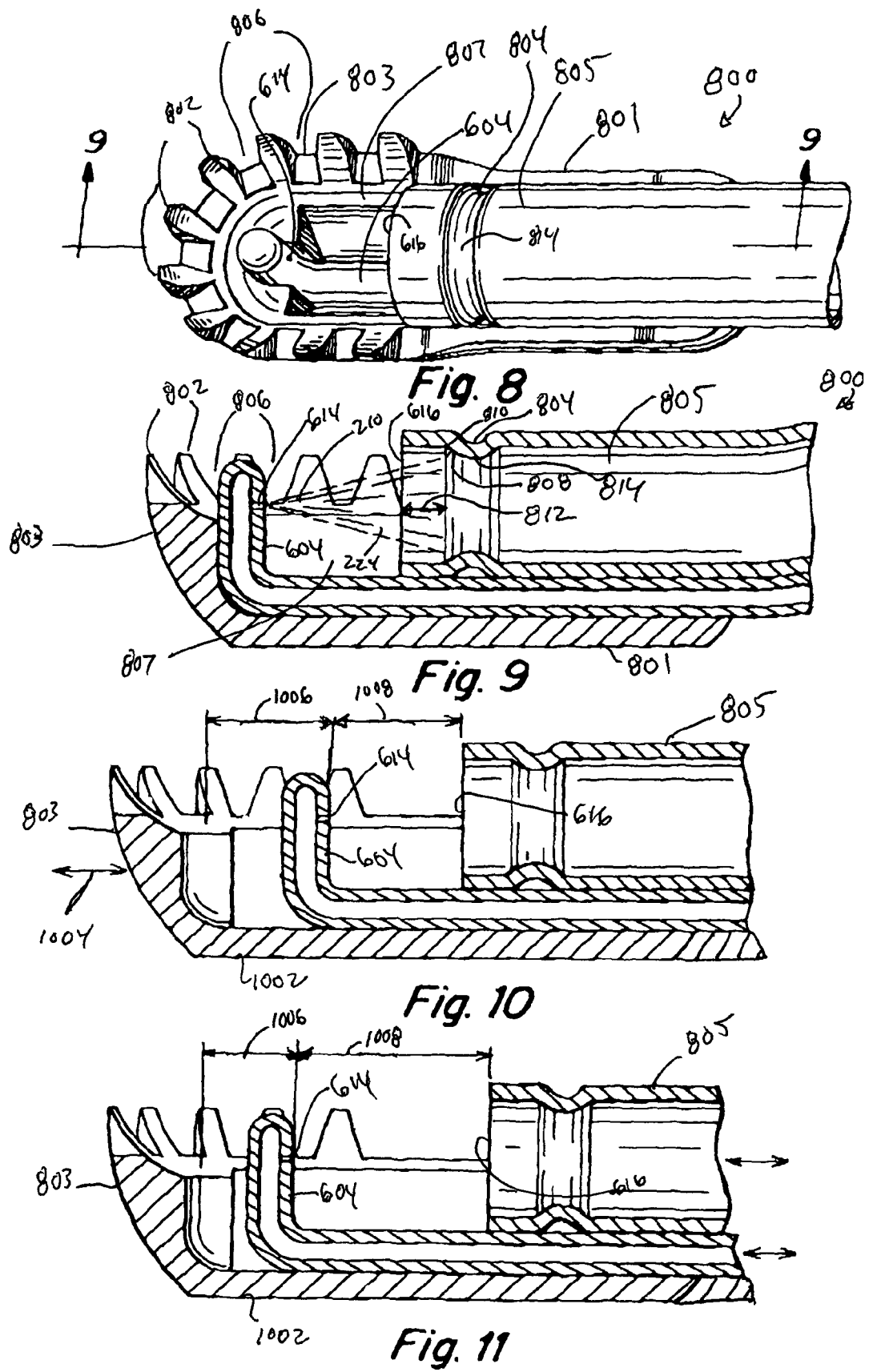

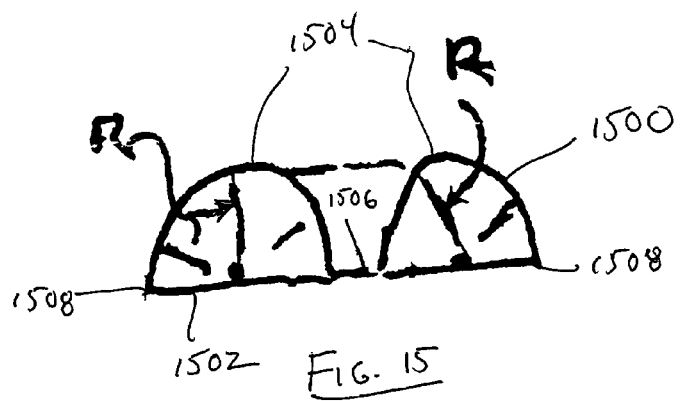
FIG. 15
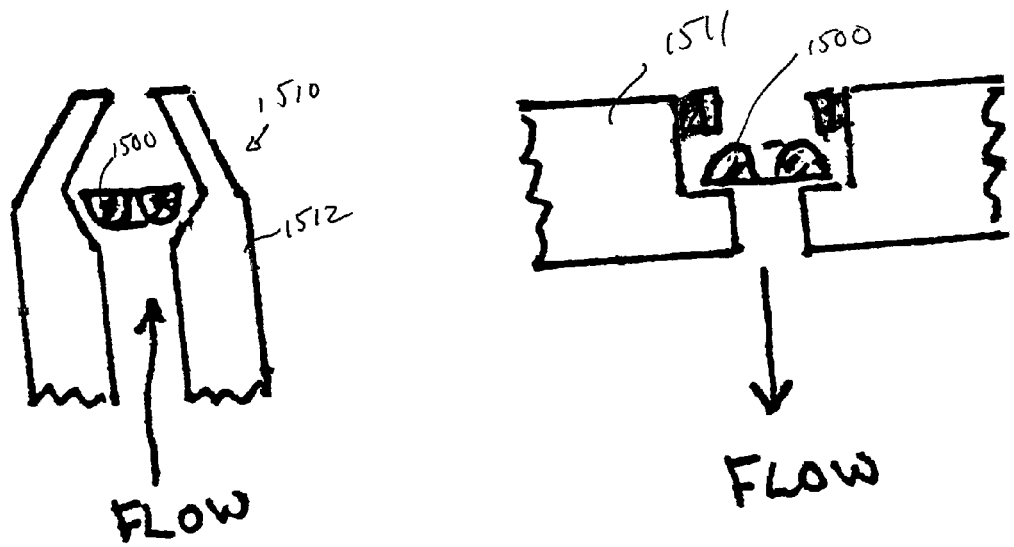
Fig. 16
Fig. 17

SURGICAL DEVICES INCORPORATING LIQUID JET ASSISTED TISSUE MANIPULATION AND METHODS FOR THEIR USE

RELATED APPLICATIONS

This non-provisional application claims the benefit under Title 35, U.S.C. §119(e) of the following co-pending U.S. provisional application Ser. Nos. 60/421,219, filed Oct. 25, 2002; 60/444,344, filed Jan. 31, 2003; and 60/488,024 filed Jul. 17, 2003; each of which is incorporated herein by reference.

BACKGROUND OF THE INVENTION

1. Field of the Invention

The present invention relates to surgical devices utilized for surgical procedures and incorporating liquid jets to assist manipulation of tissue and/or to manipulate tissue, and, more particularly to surgical devices utilizing high pressure liquid jets to cut tissue and/or drive mechanical tissue cutting components and/or remove or assist in removal of tissue from a surgical site.

2. Description of the Related Art

Surgery, especially surgery in confined spaces surrounded by delicate tissue, is very difficult to perform and requires a great degree of skill on the part of a surgeon and specialized surgical instruments. Tissue removing or manipulating surgical instruments traditionally utilized in such procedures often include specialized cutting, scooping, grasping, etc. components having particular shapes and orientations configured for specific surgical purposes. Examples of challenging surgical environments requiring specialized instruments include joints, the nasal cavity, the throat, the skull, the male and female urinary and reproductive tract, etc. One particularly challenging environment is the spine, where access to the vertebral disc often requires removal of fibrous cartilaginous tissue and vertebral bone while avoiding contact with the spinal cord, and nerves, veins and arteries embedded within or adjacent to the spinal column.

While a variety of tissue cutting/removal instruments can be utilized in one or more of the above-mentioned surgical environments, most such instruments can generally be classified as those whose tissue cutting/removal component is stationary with respect to the rest of the instrument and those with sliding, rotating, or otherwise movable tissue manipulating components. While each class includes many instruments, for illustrative purposes, the term "curette" will be utilized to represent the former class and the term "rongeur" will be utilized to represent the later class. As will be apparent to those skilled in the art based on the description of the invention to follow, many other traditional surgical instruments share one or more of the shortcomings discussed below and would benefit from the disclosed invention.

A curette is a well-known surgical device typically comprising a handle and a cup-shaped or ring-shaped distal operating end, typically with sharpened, tissue-cutting edges (see FIG. 1). In use, a curette is typically dragged across and/or pushed into tissue to score and remove tissue. In certain applications, a curette is used to remove a softer superficial layer or quantity of tissue from a harder tissue, such as bone. An example of use in surgery includes the scraping of cartilage from bony surfaces of the spine to promote fusion of a disc implant to vertebrae.

When typical conventional curette devices are employed, the surgeon, upon excising a piece of tissue, must usually remove the entire instrument from the surgical area and remove the excised tissue from the instrument prior to reinsertion of the instrument into the surgical area to excise more tissue. Such a process is tedious, fatiguing to the surgeon, and exposes the patient to an increased risk of damage to delicate tissues within the surgical area.

Thus, while the basic shape and function of the conventional curette, and similar instruments, is desired by many surgeons for many purposes, an improved means of facilitating tissue removal from the surgical site and/or improved tissue cutting for such instruments is desirable.

A rongeur is an instrument, typically for excising hard tissue, such as cartilage and bone, often characterized by distal end including a mechanical cutting or punching component actuatable by manipulating the handle of the instrument, e.g. by squeezing, scissor action, etc. Many rongeurs and bone punches utilized for spine surgery are configured to include a tube having a sharpened distal end that is longitudinally moveable to contact the proximal side of a bone/tissue protrusion and cut/snip/punch the protrusion upon actuation with the handle (see FIG. 12). If bone or cartilage is present between the tube and the protrusion, it can be cut and locally retained, with sufficient precision that damage to adjacent tissue, particularly the spinal cord, can reliably be avoided. However, the cut piece of bone or other tissue cannot safely be released inside the confines of the spine. Hence, the instrument must be removed after each cut; the cut piece deposited appropriately; and the instrument re-inserted. This makes the removal of tissue time-consuming, tedious, and physically demanding for the surgeon, particularly in terms of fatigue of the hand and also increases trauma to the patient and increases the risk of damage to sensitive surrounding tissue. Similar considerations apply in surgery of the skull, or in surgery adjacent to nervous tissue in any area of the body, particularly when involving removal of mechanically strong tissues such as bone, cartilage or calcified tissue. Great delicacy and precision are also required in other types of surgery, including surgery of the reproductive tract, the urinary tract, the upper respiratory system including the nose and the sinuses, the visual system, and the auditory system. Thus, there is a need for improved means of providing for tissue removal and/or tissue cutting for these and similar instruments.

In addition, other conventional, powered tissue removal instruments, such as drills and rotary cutting burrs, etc. are not generally considered sufficiently safe for use in many of the above-mentioned challenging surgical environments, since any operator error using conventional forms of such devices can result in damage to the spinal cord, nerves, blood vessels, or other delicate tissues of the patient. There is a need for instruments that can reliably remove tissue in proximity to delicate tissue, as described above, with greater speed, efficiency, and less trauma to the patient, and with less physical stress on the surgeon's hand and forearm musculature.

SUMMARY

Surgical instruments are disclosed that utilize high-pressure liquid jets to perform a variety of useful functions. In certain embodiments, surgical instruments are described incorporating one or more liquid jets utilized to contact tissue excised by a non-liquid jet tissue-cutting component of the surgical instrument for the purpose of further cutting the excised tissue and/or fragmenting and/or disaggregating at least a portion of the excised tissue into a plurality of small particles and/or facilitating or assisting removal of excised tissue from a surgical site without the need to remove the instrument from the surgical site. In certain embodiments, a liquid jet of a surgical instrument can be utilized for the purpose of excising tissue of a patient immobilized and/or manipulated by the surgical instrument. Also described are surgical devices of the type characterized by curettes, rongeurs, bone punches, bone cutting forceps, morcellators, surgical micrograspers, with functionality and performance supplemented by the integration of a liquid jet. The liquid jet, in certain embodiments of such instruments, can be used, for example, as a cutting jet and/or as a power source for a rotary tissue-contacting device, such as a drill or burr abrader. In certain embodiments, the liquid jet provided in the inventive instruments can be used to bring about or speed up the piece-wise removal of tissue, for example bone or a nucleus of a spinal disc, by converting at least a portion of a segment of tissue excised with the device into smaller particles in situ and removing them. In operations such as those on the spine, e.g. as in the repair of herniated discs, functionality provided by liquid jets of certain of the inventive instruments can facilitate excision of tissue and removal of the excised tissue from the surgical site while requiring less/no movement of the instrument to discharge debris from the operative site, thereby improving the speed and safety of operation and decreasing fatigue and workload for the surgeon. Also disclosed are methods of using certain liquid jet-containing surgical instruments for performing surgical procedures, for example surgical procedures on the spinal column of a patient.

In one aspect of the invention, surgical instruments are disclosed. In one embodiment, the surgical instrument comprises: a nozzle that is shaped to form a liquid jet; a pressure lumen configured and positioned to convey a flow of liquid to the nozzle; an evacuation lumen comprising a jet-receiving opening locatable opposite the nozzle to receive at least a portion of the liquid jet emitted from the nozzle, when the instrument is in operation, and which is configured and positioned to convey a flow of liquid away from the jet-receiving opening; and a non-liquid jet tissue-cutting component constructed and positioned to excise tissue during the surgical procedure, wherein the nozzle is positioned, during operation of the instrument, to direct the liquid jet so as to contact tissue excised by the non-fluid jet tissue-cutting component during a surgical procedure.

In another embodiment, the surgical instrument comprises: a nozzle that is shaped to form a liquid jet; a pressure lumen configured and positioned to convey a flow of liquid to the nozzle; an evacuation lumen comprising a jet-receiving opening locatable opposite the nozzle to receive at least a portion of the liquid jet emitted from the nozzle, when the instrument is in operation, and which is configured and positioned to convey a flow of liquid away from the jet-receiving opening; and a non-liquid jet, non-rotating tissue-cutting component constructed and positioned to excise tissue during the surgical procedure.

In yet another embodiment, the surgical instrument comprises: a non-liquid jet tissue-cutting component constructed and positioned to excise tissue during a surgical procedure; a tissue receptacle configured and positioned to contain tissue excised by the tissue-cutting component; a nozzle that is shaped to form a liquid jet and is positioned to direct the liquid jet so that at least a portion of the liquid jet is contained within the receptacle, when the instrument is in operation; and a pressure lumen configured and positioned to convey a flow of liquid to the nozzle.

In yet another embodiment, the surgical instrument comprises: a cup-shaped tissue receptacle configured and positioned to contain tissue; a nozzle that is shaped to form a liquid jet and is positioned to direct the liquid jet so that at least a portion of the liquid jet is contained within the receptacle, when the instrument is in operation; and a pressure lumen configured and positioned to convey a flow of liquid to the nozzle.

In yet another embodiment, the surgical instrument is a curette, a rongeur, a bone punch, bone-cutting forceps, a morcellator, or a surgical micrograsper and comprises: a nozzle that is shaped to form a liquid jet; and a pressure lumen configured and positioned to convey a flow of high-pressure liquid at a pressure of at least 1,000 psig to the nozzle.

In yet another embodiment, the surgical instrument is a curette device comprising: a nozzle that is shaped to form a liquid jet and a pressure lumen configured and positioned to convey a flow of liquid to the nozzle.

In yet another embodiment, the surgical instrument comprises: a distal end of the instrument adapted to perform a surgical procedure on a patient and comprising a tissue manipulating component configured and positioned to manipulate a tissue of the patient; a proximal end of the instrument having at least a portion thereof configured to be grasped and/or manipulated by an operator, said portion of the proximal end being operatively coupled to the tissue manipulating component of the distal end to facilitate control and actuation of the tissue manipulating component from a non-manipulating configuration to a manipulating configuration by manipulation of said portion of the proximal end by the operator; a nozzle that is shaped to form a liquid jet; and a pressure lumen configured and positioned to convey a flow of liquid to the nozzle, wherein the nozzle is constructed positioned, during operation of the instrument, to direct the liquid jet to fragment and/or disaggregate and/or cut of at least some tissue manipulated by the manipulating component.

In yet another embodiment, the surgical instrument comprises: a distal end adapted to perform a surgical procedure on a patient and a proximal end adapted to facilitate control of the instrument by an operator; a rotatable tissue-contacting component constructed and arranged for contact with tissue in a surgical operating field and located at the distal end; a nozzle that is shaped to form a liquid jet; a pressure lumen configured and positioned to convey a flow of liquid to the nozzle; a liquid jet-driven rotor configured and positioned with respect to the nozzle to be drivable in rotation by the liquid jet formed by the nozzle and operatively coupled to the rotatable tissue-contacting component, when the instrument is in operation, such that rotation of the liquid jet-driven rotor causes rotation of the rotatable tissue-contacting component, wherein at least one of the rotatable tissue-contacting component and a distal-most end of the surgical instrument is longitudinally movable relative to the other upon manipulation of at least a portion of the proximal end of the instrument by the operator.

In another aspect of the invention, methods of performing a surgical procedure on a patient are disclosed. In one embodiment, the method comprises: applying a surgical instrument to a surgical site of the patient; excising a piece of tissue from the patient with a non-liquid jet tissue-cutting component of the surgical instrument; and directing a liquid jet associated with the surgical instrument towards the piece of tissue excised in the excising step so that the liquid jet impacts the piece of tissue.

In another embodiment, the surgical method comprises: applying a surgical instrument comprising a liquid jet to the spine of the patient; and excising tissue from the spine of the patient with the surgical instrument.

In yet another embodiment, the surgical method comprises: applying a curette to a surgical site of the patient; and creating a liquid jet associated with the curette.

BRIEF DESCRIPTION OF THE DRAWINGS

The accompanying drawings are schematic and are not intended to be drawn to scale. In the figures, each identical, or substantially similar component that is illustrated in various figures is typically represented by a single numeral or notation. For purposes of clarity, not every component is labeled in every figure, nor is every component of each embodiment of the invention shown where illustration is not necessary to allow those of ordinary skill in the art to understand the invention.

In the drawings:

FIG. 1 is a schematic perspective illustration of a conventional curette surgical instrument;

FIG. 2 is a schematic perspective illustration of a surgical instrument comprising a liquid jet-assisted curette, according to one embodiment of the invention;

FIG. 3 is an enlarged detail perspective view of the distal end of the liquid jet-assisted curette of FIG. 2;

FIG. 4 is a cross-sectional side view of the instrument of FIG. 3b taken along lines 4-4;

FIG. 5 is a cross-sectional side view similar to FIG. 4, except showing an alternative embodiment for positioning the jet nozzle in the instrument;

FIG. 6 is an enlarged detail perspective view of the distal end of a liquid jet-assisted curette similar to that illustrated in FIG. 2, except having a differently configured cup/evacuation lumen/pressure lumen assembly;

FIG. 7 is an exploded perspective view of the distal end illustrated in FIG. 6;

FIG. 8 is an enlarged detail perspective view of the distal end of a liquid jet-assisted curette similar to FIG. 6, showing another embodiment for configuring the curette cup and evacuation lumen;

FIG. 9 is a cross-sectional side view of the distal end illustrated in FIG. 8 taken along lines 9-9;

FIG. 10 is a cross-sectional side view of a distal end similar to that illustrated in FIG. 8, except showing a first embodiment of providing for adjustment of the longitudinal position of the nozzle and evacuation lumen opening with respect to the distal end of the cup;

FIG. 11 is a cross-sectional side view of a distal end similar to that illustrated in FIG. 8, except showing a second embodiment of providing for adjustment of the longitudinal position of the nozzle and evacuation lumen opening with respect to the distal end of the cup;

FIG. 15 is a schematic cross-sectional view of a nozzle insert for forming certain liquid jet-forming nozzles of the instruments of the invention;

FIG. 16 is a schematic cross-sectional view of a first embodiment of a nozzle incorporating the nozzle insert illustrated in FIG. 15;

FIG. 17 is a schematic cross-sectional view of a second embodiment of a nozzle incorporating the nozzle insert illustrated in FIG. 15;

DETAILED DESCRIPTION

Figure 12:
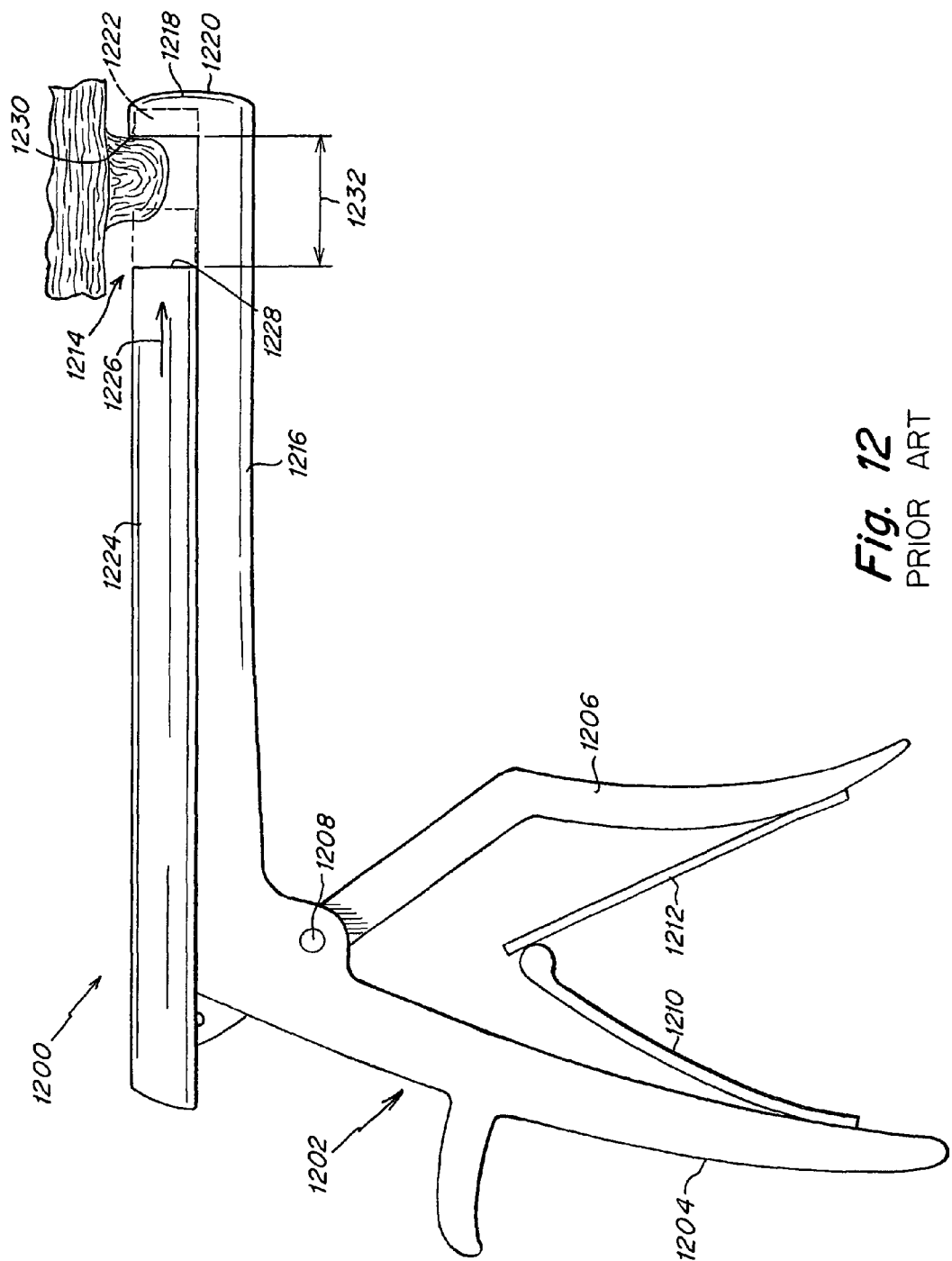
FIG. 12 is a schematic side elevational view of a conventional rongeur-type surgical instrument.

The surgical instruments provided according to certain embodiments of the invention can take on many configurations, depending on the particular application and in the particular surgical arena in which they are intended to be used. In one series of embodiments, surgical instruments are disclosed that comprise a basic form and functionality similar to well-known and well-accepted surgical handpiece instruments for tissue removal and/or manipulation, except that they are configured to include one or more high pressure liquid jet components configured to assist and/or enhance their traditional functionality and/or provide new functionality.

As described in more detail below, in certain embodiments, the liquid jet-forming components provided according to the invention are configured with respect to the other components of the inventive surgical instruments such that one or more high pressure liquid jets formed by the instruments are positioned and configured to cut and/or fragment and/or disaggregate and/or facilitate removal of excised tissue of a patient. In certain embodiments, the liquid jet acts through direct contact with the tissue, while in other embodiments it acts through utilization of the liquid jet to power other tissue-cutting or tissue-manipulating components of the surgical instrument. In yet other embodiments, one or more liquid jets can be provided, such that liquid jets of the instrument can act through both of the above-mentioned modes of action.

In certain embodiments, the invention involves incorporating high pressure liquid jet-forming components into surgical instruments designed for use in confined spaces surrounded by delicate tissue; for example, the spine, joints, the nasal cavity, the throat, the skull, the male and female urinary and reproductive tracts, etc. Also, as would be apparent to those skilled in the art, the inventive features and functionality described below may be readily adapted, using no more than routine skill and experimentation, for use in a wide variety of surgical instruments specifically designed for surgery in the locations described immediately above, and in other locations, which are not specifically called out, described, or illustrated in the figures herein. Accordingly, the specific, exemplary instruments illustrated and described herein incorporating the below-described inventive liquid jet components must be considered to be merely a small subset of the multitude of configurations and other instruments which would benefit from the inventive components and functionalities and which the skilled artisan would be able to adapt to include such components and functionalities using no more than ordinary skill in the art. Accordingly, all such instruments and configurations, which are within the scope of the appended claims, form part of the present invention, even if not explicitly described herein.

In many embodiments, and for many applications, the inventive surgical instruments can comprise a surgical handpiece with a body and/or handle designed to be gripped by the hand of an operator during a surgical or medical procedure. In other embodiments, the inventive surgical instrument could be configured to be operated by a robotic positioning machine or other type of machine-based positioning/manipulation device. Such hand pieces can be configured for use in open surgical procedures or, alternatively, can be configured in use in laparoscopic- or endoscopic-type procedures. In yet other embodiments, rather than being of the form of a hand piece-type instrument, surgical instruments of the invention could take on other configurations known to those skilled in the art.

Surgical instruments described herein typically will typically include a "distal end" and a "proximal end." A "distal end" of a surgical instrument, as used herein, refers to that portion of the instrument that is adapted to perform a surgical procedure on a patient. The "distal end" typically includes such structure as a tissue-manipulating component configured and positioned to manipulate a tissue of the patient, which in certain embodiments can comprise a tissue-cutting component. In certain embodiments, a liquid jet-forming nozzle may also be provided at the distal end of the surgical instrument, as illustrated and described in more detail below. While the distal end is typically located at a position on the instrument farthest from the operator during use, (i.e., a distal-most position), this need not always be the case.

The "proximal end" of the instrument refers to that portion of the instrument adapted to be controllable by an operator of the instrument. For embodiments wherein the instrument comprises a surgical handpiece, the proximal end typically will include a body and/or handle configured and adapted to be grasped by the hand of an operator during use and which may, in some embodiments, be operably coupled by mechanical, electrical, or other operative coupling, to a tissue-manipulating/cutting component at the distal end of the instrument to facilitate control and/or actuation of such component (e.g., from a non-manipulating configuration to a manipulating configuration) upon manipulation of the handle/body by the operator.

Throughout the present discussion, the inventive surgical instruments are typically referred to as including "liquid jet-" forming components or providing one or more "liquid jets." It should be understood that, while, in certain embodiments use of liquids to form the liquid jet is preferred, in alternative embodiments, surgical instruments according to the invention could utilize fluids other than liquids, such as certain gasses. Accordingly, wherever "liquid" or "liquid jet" is indicated, the terms "fluid" (encompassing both liquids and gasses) and "fluid jet," respectively, should also be inferred as being equivalent, unless otherwise specified. In addition, the use of the term "high pressure" as descriptive of the liquid provided by the instrument, in forming the liquid jets of certain embodiments of the surgical instruments of the invention refers to the pressure of the liquid, at the position of the jet opening of a liquid jet-forming nozzle of such instrument, being at least about 500 psig. In certain embodiments of the inventive surgical instruments, the high-pressure liquid supplied to a liquid jet nozzle of the instrument will have a pressure of at least 1,000 psig, in other embodiments at least 2,000 psig, in other embodiments at least 3000 psig, in other embodiments at least 5,000 psig, in other embodiments at least 10,000 psig, in other embodiments at least 15,000 psig, in other embodiments at least 30,000 psig, and in yet other embodiments up to about 50,000 psig, or more. In certain embodiments the high-pressure liquid supplied to a liquid jet nozzle of the instrument will have a pressure will have a pressure in the range of 2,000-15,000 psig, in other embodiments between 5,000-10,000 psig, in yet other embodiments between 5,000-7,500 psig, and in yet other embodiments between about 2,000 and 5,000 psig.

Certain embodiments of the inventive surgical instruments incorporating liquid jets are advantageously configured to be utilized in surgical procedures, such as certain surgeries on the spine, involving the excision and removal of tissue from patients in a surgical site surrounded by delicate tissue. Accordingly, in certain such embodiments, the liquid jet functionality provided according to the invention is configured and adapted to be utilized as part of a surgical instrument having a configuration, shape, size and contour specifically adapted for use in such applications. An incomplete list of surgical instruments that can be adapted to include a liquid jet-forming component according to the invention, and which constitutes an exemplary list of certain embodiments of surgical instruments provided according to the invention, includes curettes, rongeurs, bone punches, bone-cutting forceps, morcellators, and surgical graspers or micrograspers (such as certain clamps, forceps, etc.). According to the invention, instruments in the form of those described above are constructed to include a nozzle that is shaped to form a liquid jet, and a pressure lumen that is configured and positioned to convey a flow of high pressure liquid to the nozzle. The form, construction, size and shape, contour, and other aspects of the design of the above-mentioned surgical instruments, without inclusion of the above-mentioned inventive liquid jet-forming nozzle, are well known in the art and are described in many textbooks of surgery, surgical catalogs, and other sources; for example, the reader is referred to "The Orthopedic Sourcebook" published by KMedic, and available for download at their web site: www.kmedic.com, for a description and illustration of many such instruments. It is one feature of certain embodiments of the present invention that, in the inventive surgical instruments provided with liquid jet-forming components, the basic shape, size, contour, and basic functionality of such known, accepted, and useful surgical instruments is maintained, while the performance, utility, efficiency, and safety of the instruments can be enhanced through the inventive provision of such a liquid jet-forming components.

In certain embodiments of the invention, the inventive surgical instruments are provided with a liquid jet-forming nozzle, that is constructed and positioned within the instrument so as to direct a liquid jet in such a manner that it fragments and/or disaggregates and/or cuts some tissue manipulated by a tissue-manipulating component at the distal end of the instrument, either through direct contact with the tissue or through indirect means, such as by powering a tissue contacting component positioned at the distal end of the instrument. For example, in certain embodiments, the liquid jet-forming nozzle may be positioned at the distal end of the instrument so that it directs the liquid jet so as to impact, cut, and/or fragment and/or disaggregate tissue acted upon by a tissue-manipulating component such as, for example, a cutting blade, grinding burr, tissue punch, forceps, clamp, grasper, etc. In other embodiments, the liquid jet-forming nozzle may be positioned within the instrument such that the liquid jet formed by the nozzle does not contact tissue but, rather, is utilized as a source of force and energy for powering a tissue cutting component at the distal end of the instrument. An example of such an embodiment includes an instrument having a liquid jet-powered grinding burr, drill, rotating cutting blade, etc. as part of its structure. (See, for example, FIGS. 18-20, described in more detail below). A "tissue manipulating component" as used in the above context refers to any structure that is able to bring about a change in at least one physical property of tissue by applying a physical or non-physical force (e.g., electrical energy, electromagnetic radiation, etc.). Specific examples of tissue manipulating components that can be utilized in some surgical instruments include components configured to cut, grasp, excise, grind, puncture, or burn tissue in a surgical field.

In one series of embodiments, surgical instruments, according to the invention, include a tissue-manipulating component that comprises a non-liquid jet tissue-cutting component that is constructed and positioned to excise tissue during a surgical procedure. Such instruments are exemplified by, for example, sharpened cutting curettes, certain rongeurs, bone punches, etc. A "non-liquid jet tissue-cutting component," as used herein, refers to essentially any component configured and provided for cutting tissue, other than by impacting the tissue with a high pressure liquid jet. Examples include, but are not limited to, mechanical cutters such as blades, piercing devices, scissors, punchers, grinders, shavers, etc., and non-mechanical tissue cutters such as electrosurgical electrodes, lasers, etc. In certain such embodiments, the non-liquid jet tissue-cutting component is stationery and in a fixed positional relationship to the handle/body and the rest of the surgical instrument (e.g. as in typical curettes), while, in other instruments, the non-liquid jet tissue-cutting component can be configured to be movable with respect to the body/handle or some other portion of the instrument (e.g. as in certain rongeurs, bone punches, etc.). In certain such embodiments, the non-liquid jet tissue-cutting component will be longitudinally moveable within the instrument (e.g. movable in a sliding fashion along an axis parallel to a longitudinal axis of the distal end of the instrument), but will be configured to "non-rotatable" or "non-rotating," (i.e. will not be able to rotate 360 degrees or more about its own longitudinal axis).

In certain of the above-described surgical instruments, the nozzle of the instrument will be positioned, at least during operation of the instrument, to direct a liquid jet formed by the nozzle so that it contacts tissue excised by a non-liquid jet tissue-cutting component of the instrument during the surgical procedure. Such contact by the liquid jet can, in certain embodiments, do either or both of enhance the cutting action of the non-liquid jet tissue-cutting component and facilitate disaggregation of tissue excised by the non-liquid jet tissue-cutting component. In addition, as described below in further detail, for certain embodiments of the inventive surgical instruments, which include an optional evacuation lumen configured for removing tissue and debris, the liquid jet can be positioned so that a jet-receiving opening of the evacuation lumen is locatable opposite the nozzle so that it is positioned to receive at least a portion of the liquid jet, and preferably essentially the entire liquid jet, that is emitted from the nozzle when the instrument is in operation. In such embodiments, the liquid jet can be used to advantageously facilitate and/or assist in removal of both liquid and tissue/debris from the operative site, without the need for removing the entire instrument from the operative site.

As mentioned above, in certain embodiments of the surgical instruments provided according to the invention, a liquid jet-forming nozzle is positioned within the instrument to enable the liquid jet to contact tissue excised or otherwise manipulated by a tissue-manipulating component at the distal end of the instrument. In certain such embodiments, the surgical instruments may also include, at the distal end, a tissue receptacle that is configured and positioned to contain tissue manipulated or excised by the tissue-manipulating component. In such embodiments, the nozzle of the instrument can be positioned to form a liquid jet having at least a portion thereof that is contained within the receptacle, when the instrument is in operation. Accordingly, the liquid jet can serve to cut, fragment, and/or disaggregate, and/or facilitate removal of tissue excised and contained in the receptacle in certain such instruments. A "tissue receptacle" as used in the above context refers to any structure that is able to contain, surround, and/or immobilize tissue. In certain embodiments, a tissue receptacle may be cup-shaped, such as is the case in many curette-type instruments. In other embodiments, the tissue receptacle may be in the shape of a conduit (i.e. conduit-shaped), such as may be the case for surgical instruments such as certain rongeurs and bone punches, wherein the tissue receptacle can comprise a distal cutting end of a sliding tube (See e.g. FIGS. 13 and 14). "Conduit-shaped," as used herein within the context of describing the configuration of certain tissue receptacles, refers to such receptacles being in the shape of a tube, duct, or channel, which is able to permit fluid to flow along and through at least a portion of a lumen of the receptacle.

It should be clear from the above general discussion of the attributes of various surgical instruments within the scope of the present invention that an extremely wide variety of instruments can be readily provided with the inventive functionality and components described herein, and that it is not feasible to illustrate and describe in detail every possible example of such instruments. Accordingly, solely for the purpose of illustrating various features and properties of the inventive surgical instruments and to provide guidance to those skilled in the art as to how to construct and configure instruments provided according to the invention, reference will be made to two particular types of instruments, which are illustrated and described in detail below. Specifically, as mentioned in the background section, curette-type instruments are representative of a class of surgical instruments having a tissue manipulating/cutting component that is stationary with respect to the rest of the instrument, and a spinal rongeur/bone punch of the Kerrison handle type exemplify instruments including tissue manipulating/cutting components that are movable with respect to some part/component of the instrument and which are able to be actuated by an operator via manipulation of a handle or other component at the proximal end of the instrument.

At the outset, it should be noted that a detailed treatment and discussion of a wide variety of design parameters, configurations, materials of construction, and other aspects of the design, fabrication, and construction of liquid jet surgical instruments are provided in commonly owned U.S. Pat. Nos. 5,944,686; 6,375,635; and 6,511,493; and in U.S. Patent Application Publication Numbers 2003/0083681 A1 and 2003/0125660 A1, each of which is incorporated herein by reference. The reader is referred to these issued patents and patent publications for detailed description of and guidance as to the construction and design of certain embodiments of the liquid jet components of the instruments described herein. For example, U.S. Pat. No. 6,375,635 describes in detail design considerations related to the configuration and sizing of the nozzle, evacuation lumen, liquid jet length and dispersion, materials of construction, liquid pressures for operation, etc. for liquid jets configured to directly contact, cut and/or fragment and/or disaggregate tissue and facilitate removal of tissue through an evacuation lumen. U.S. Pat. No. 6,511,493 and U.S. Patent Application Publication Number 2003/0125660 A1 describe in detail configurations and design considerations for constructing liquid jet impact-driven rotors for powering rotational elements, such as grinding burrs, drills, etc. in surgical instruments. Accordingly, while certain specific design parameters are called out and discussed in more detail below, others that may not specifically mentioned or discussed are discussed in detail in one or more of the above-referenced U.S. patents or Patent Publications. Such parameters, configurations and design considerations disclosed in these references can be, in many cases, applicable to and useful for practicing many aspects of the current invention.

Regarding the overall shape, size, configuration, and structure of the surgical instruments described herein—other than the components specifically utilized for providing the liquid jet functionality—these are preferably made to be the same as, or approximating as closely as possible, those of typical, conventional surgical instruments of the same or similar type. Configuration, size, geometry, etc. of such instruments vary widely depending on their particular application, and typically a wide variety of each type of instrument is commercially available. For a description of the configuration and features of such traditional instruments, which design and configuration is preferably duplicated or approximated in the inventive instruments, the reader is referred to the above-referenced "Orthopedic Sourcebook."

Reference is now made to FIGS. 1-5 illustrating both a conventional curette surgical device (FIG. 1) and one embodiment of a liquid jet-assisted surgical curette according to the invention. Referring to the prior art curette device illustrated in FIG. 1, curette 100 includes a proximal end including a handle 102, an elongated neck region 104, and distal end including a tissue-manipulating component 106. In the illustrated embodiment, tissue manipulating component 106 comprises a cup-shaped tissue receptacle. In other embodiments, not shown, the tissue manipulating component at the distal end of the curette may not be cup- or scoop-shaped, as illustrated, but rather could take many other forms. For example, in certain embodiments, component 106 could be ring-shaped. As mentioned previously, a wide variety of curette instruments including a wide variety of differently configured and shaped tissue cutting or tissue manipulating components useful for different purposes and in different surgical procedures are known in the art.

Cup-shaped tissue receptacle 106 typically will have a sharpened peripheral rim 108 comprising a tissue-cutting component, which can be used to scrape, cut, and/or excise tissue with the instrument. The angle 109 formed between the longitudinal axis 110 of cup 106 and longitudinal axis 112 of the proximal portion of neck 104 and handle 102 can vary over a wide range for different instruments. For example, in certain embodiments, angle 109 could potentially vary within the range from about 0 degrees to about 90 degrees. As illustrated, angle 109 is about 30 degrees.

The width 111 and length 113 of cup 106, and the depth and shape of the receptacle formed by depression 114 of cup 106, can also vary over a wide range depending on the particular instrument and application. For certain typical instruments, width 111 and length 113 of cup 106, and the depth of the receptacle formed by depression 114 of cup 106 is within the range of a few millimeters, for example between about 2-8 millimeters. As illustrated, the shape of cup 106 is somewhat oval having a length 113 exceeding width 111. However, in other embodiments, the shape may be round, square, or a variety of other shapes, as would be apparent to those skilled in the art. In use, the surgeon would insert cup 106 into a surgical operating space and scrape, cut, and/or excise tissue within the space so that it is contained within depression 114. After excising tissue, the surgeon would be required to remove the curette from the operating space to remove the excised tissue contained within depression 114 and then reinsert the instrument into the operating field to harvest another piece of tissue.

FIGS. 2-4 illustrate one embodiment of a surgical instrument according to the invention comprising a liquid jet-assisted surgical curette 200. Liquid jet curette 200 is similar in overall configuration and size to curette 100. Liquid jet curette 200 can include, at its proximal end, a handle 202 and, at its distal end, a cup-shaped tissue manipulating component 206. As is shown more clearly in FIGS. 3 and 4, the distal end of curette 200 can also include a nozzle 208 positioned within cup 206 and shaped to form a liquid jet 210. As is shown in FIG. 4 and as is discussed in greater detail below, nozzle 208 can be positioned within cup 206 so as to direct liquid jet 210 so that it contacts tissue that is partially contained within cup 206 during operation. In the illustrated embodiment, the curette cup is oval having a length 113 exceeding its width 111, and is sized to fit within the disc space of the vertebra, while allowing the long side of cup edge 108 to efficiently scrape the vertebral end plates.

Instrument 200 further includes a high-pressure lumen 214 that is configured and positioned to convey a flow of high pressure liquid to nozzle 208. In the illustrated embodiment, pressure lumen 214, over most of its length, is located external to neck 204 and cup 206 portions of the instrument. Pressure lumen 214 can enter cup 206 through hole 216 therein, such that nozzle 208 is positioned within tissue receptacle 114 formed by cup 206. In certain such embodiments, pressure lumen 214 can be attached to neck 204 and/or cup 206, e.g. via welding, brazing, clamping, etc., to secure the pressure lumen in place and prevent deflection thereof during use. However, this configuration is purely optional and, for example as illustrated in FIGS. 6-11, various other configurations for positioning and securing the pressure lumen within the instrument can be utilized, as would be apparent to those skilled in the art.

In certain embodiments, the high pressure liquid conveyed by pressure lumen 214 and utilized to form liquid jet 210 with nozzle 208 will comprise a saline solution or other physiologically compatible liquid. Pressure lumen 214, at the proximal end of instrument 200, can be contained within handle 202 and can be in fluid communication with high pressure supply line 220 supplying a source of high pressure liquid.

It should be noted that in the embodiment illustrated, the distal end of pressure lumen 214 includes a hole therethrough comprising nozzle 208. Such a hole can be formed, for example, by drilling or etching. It should be noted that the illustrated configuration of a hole in the distal end of high pressure lumen 214 forming the nozzle 208 is merely exemplary, and that a wide variety of other techniques for forming the nozzle can be utilized. A number of such techniques and exemplary nozzles formed thereby, which can be used in certain embodiments of the present invention, are described in commonly-owned U.S. Pat. No. 6,375,635.

In general, the nozzles of the inventive surgical instruments can be formed in the high pressure lumen by any means known to those of ordinary skill in the art. The diameter and shape of the jet opening 222 of the nozzle 208 is selected and determined based upon the desired cross-sectional diameter of the liquid jet formed by the instrument and can vary depending upon the particular applications and uses of the instrument. In certain typical embodiments, the diameter of the jet opening of the nozzle can vary within a range of from about 0.001 inch to about 0.01 inch. In one particular embodiment, the diameter of jet opening 222 of nozzle 208 is about 0.005 inch.

As discussed in commonly owned U.S. Pat. No. 6,375,635, another consideration when forming the nozzle concerns the ratio of the minimum diameter of the nozzle to the total length of the nozzle having such minimum diameter as measured along the center line of the nozzle (the "nozzle length" or "characteristic length of the nozzle"). In general, the greater is the ratio of this characteristic length of the nozzle to the minimum diameter of the nozzle, the greater is the degree of coherence of the jet formed by the nozzle and the lesser is the degree of dispersion of the jet with distance from the jet opening of the nozzle, but also the greater is the pressure drop across the nozzle. As explained in detail in the above-referenced U.S. Pat. No. 6,375,635, the selection of the nozzle length to diameter ratio and of the degree of the coherence of the liquid jet depend upon factors such as the total length of the liquid jet and the size of an inlet opening or minimum diameter opening of the evacuation lumen, when an evacuation lumen is provided, and whether the instrument is configured to be used in a surrounding air environment or submersed in a liquid environment. The reader is referred to the above-referenced commonly owned U.S. Pat. No. 6,375,635 for guidance and direction in selecting these and other parameters related to the performance of the liquid jet components provided by the inventive surgical instrument. Certain nozzles provided in the instruments of the invention can have a characteristic ratio of nozzle length to minimum jet opening diameter of from between about 1:1 to about 10:1. In one exemplary embodiment, wherein the instrument is designed for use in a surrounding gaseous environment, the nozzle has a characteristic ratio of nozzle length to minimum jet opening diameter of about 3:1.

As is shown most clearly in FIGS. 3 and 4, nozzle 208 formed in pressure lumen 214 can be configured to emit a jet of liquid into cup 206 of curette device 200. High pressure jet 210 can create an entrainment region 224 (dotted lines) of rapidly moving liquid spray as it disperses along its length. The jet can be directed to pass through at least a portion of the cup and enters a jet receiving opening 226 of an optional evacuation lumen 228, which, in the illustrated embodiment, comprises a hollow neck portion 204 of the instrument. Evacuation lumen 228 can be shaped and positioned such that jet receiving opening 226 is located opposite the nozzle and sized so as to receive at least a portion of the liquid jet emitted from the nozzle. It is preferably further configured and positioned within the instrument to convey a flow of liquid away from the jet receiving opening toward the proximal end of the instrument.

As is discussed in detail in commonly owned U.S. Pat. No. 6,375,635, the cross-sectional diameter of the jet receiving opening can be selected to enable it to be large enough to receive essentially all of the liquid comprising the liquid jet (i.e. at least as large as the diameter of the entrainment region 224 at its point of entry into the evacuation lumen). This can prevent "blow by" and misdirection of the liquid in the entrainment region. In certain embodiments, the evacuation lumen can be sized, configured, and positioned with respect to the nozzle so as to enable fluid and debris entrained by the liquid jet to be evacuated through the evacuation lumen and away from the surgical site without the need to apply an external source of suction, such as a vacuum pump, in fluid communication with evacuation lumen 228. Design considerations enabling such operation are discussed in detail in the above-referenced U.S. Pat. No. 6,375,635.

Evacuation lumen 228, in this illustrated, exemplary embodiment, comprises a hollow neck portion 204 of the instrument. However, in alternative embodiments, an evacuation lumen could comprise a separate tube affixed to a solid neck portion of a handle, for example neck portion 104 of instrument 100. In such an alternative embodiment, it can be possible to take a conventional, non-liquid jet curette that is commercially available from a variety of sources, and simply modify this curette by attachment of a pressure lumen and nozzle configuration, as illustrated in FIG. 2, and a separate evacuation lumen. Such an alternative embodiment could also be configured so that the pressure lumen/nozzle combination and/or the evacuation lumen could be separable from the rest of the instrument and disposable after a single use, while the remainder of the instrument could be sterilized and reused.

Certain exemplary embodiments of an illustrated curette instrument 200 (including a nozzle 208 having a ratio of length to minimum diameter of 3:1 as previously described and operable in an air environment and able to evacuate liquid and debris through evacuation lumen 228 and evacuation tube 230 connected thereto within body 202 of the instrument) has the following design parameters: the pressure of the liquid supplied to the nozzle is between about 5,000 psig and about 15,000 psig; the pressure lumen comprises a stainless steel hypotube having an outer diameter of about 0.045 inch and an inner diameter of about 0.020 inch; the evacuation lumen has smallest diameter opening (which can be a necked region of a constriction in certain embodiments or the jet receiving opening in other embodiments) with a diameter of between about 0.010 inch and about 0.25 inch, in certain particular embodiments between about 0.015 inch and about 0.15 inch, (and in one particular embodiment about 0.118 inch—the inner diameter of the evacuation lumen proximal the minimum diameter opening and the inner diameter of evacuation tubing 230 being somewhat larger than the inner diameter of the minimum diameter opening); and the jet length (i.e. the distance between nozzle opening 222 and jet receiving opening 226) is between about 1.5 and about 6 millimeters (and in one particular embodiment between about 3-3.4 millimeters).

Referring now to FIG. 4, nozzle 208 can be positioned within cup 206 such that the nozzle is located roughly in the center of the cup. As shown in the alternative embodiment of FIG. 5, the relative position of nozzle 208 within cup 206 can be varied. In certain embodiments, the nozzle may be positioned more distally within the cup. In certain embodiments, the nozzle is closer to rim 108 (as shown in FIG. 5). Alternatively, the nozzle is positioned more proximally and, in certain embodiments, closer to the jet-receiving opening 226 of evacuation lumen 228 (FIG. 4). The relative positioning of the jet nozzle within the cup can affect the way in which the liquid jet interacts with tissue within the surgical operating field. In certain preferred embodiments, it is desirable that the jet nozzle be oriented such that the liquid jet is directed so that a central axis of the liquid jet 232 is co-axial with the longitudinal axis 234 of at least a distal portion of evacuation lumen 228, when present. It has been found, in the context of this invention, that such an alignment can reduce the level of misting during operation of the liquid jet curette device in a surrounding air environment.

In certain embodiments, nozzle opening 222 can be positioned within curette cup 206 so that the separation distance between nozzle opening 222 and jet receiving opening 226— defining a corresponding liquid jet length—is not too large. Otherwise, the jet can tend to become blocked by excess tissue in receptacle 114 positioned proximal the nozzle, which can cause clogging of the evacuation tube. By contrast, if the separation distance and jet length is too small, excessive build-up of tissue within receptacle 114 of cup 206 distal the nozzle can occur, which can also lead to clogging of the evacuation lumen. It has been found, for certain embodiments of curette instruments having a cup-shape tissue-cutting component, that examples of a separation distance between jet opening 222 and jet-receiving opening 226, can include between about 1.5 millimeters and about 6 millimeters, between about 2 millimeters and about 4 millimeters and between about 3 millimeters and about 3.5 millimeters.

For embodiments wherein the nozzle is positioned deeper within the cup of the curette, for example as shown in FIG. 4, most of the excision of tissue 236 occurs via cutting or scraping action of rim 108 of cup 206, and the primary role of liquid jet 210 is to fragment and/or disaggregate tissue within receptacle 114 of cup 206 and drive evacuation of, or assist in evacuation of, tissue from the surgical site through evacuation lumen 228. By contrast, when nozzle 208 is positioned closer to rim 108 of cup 206, as illustrated in FIG. 5, liquid jet 210 may itself excise tissue 236 from the patient, or may assist in the excision of the tissue, by directly contacting the tissue while it is still attached to the patient (as shown in FIG. 5).

In operation, a device as illustrated in FIGS. 2-5 can be used by a surgeon in the same or a similar manner as a traditional curette. Grasping the inventive device by handle 202, the surgeon can apply cup 206 to a surgical site of the patient, for example by dragging the curette across a tissue of the patient, using edge 108 of cup 206 (which can be sharpened to form a cutting blade) to excise a piece of tissue from the surgical site. The excised tissue will tend to collect in receptacle 114 of curette cup 206. Liquid jet 210 can be continuously on during the operation, or, the hand piece 200 or another component of the fluid delivery system may be provided with an on-off switch or other control mechanism to enable the surgeon to turn the jet off and on during operation of the instrument.

In one mode of operation, as tissue is removed from the site, or after tissue accumulates in the cup, the jet is activated creating a liquid jet 210 originating from nozzle 208 and directed into jet receiving opening 226, with a corresponding entrainment region 224 of jet fluid and fluid/debris entrained by the jet. The impact of liquid jet 210 and liquid within entrainment region 224 on tissue within cup 206 can bring about fragmentation and/or disaggregation of tissue contained within the cup. The impact forces created by the high pressure liquid jet can at least partially fragment and/or disaggregate the excised tissue and entrained tissue debris. The force and momentum of the liquid jet can also, in certain embodiments, facilitate removal from the surgical site of at least a portion of the piece of tissue excised with the instrument by forcing the tissue debris and fluid proximally through evacuation lumen 228 and away from the surgical site. In certain embodiments, evacuation can be assisted via connecting a source of external suction, for example a vacuum pump, in fluid communication with evacuation lumen 228. However, in certain configurations, the instrument may be configured, as described above and/or in U.S. Pat. No. 6,675,635, to enable evacuation of the liquid comprising the liquid jet and tissue debris, without the need for an external source of suction.

In addition, in certain configurations, the action of the liquid jet can create a localized vacuum effect as the jet and entrained fluid flows through receptacle 114 and evacuation lumen 228. Such vacuum effect can further serve to assist in removing tissue from the operating site through the evacuation tube. Such a vacuum effect can also serve to draw rim 108 of cup 206 into apposition to the tissue being cut. In certain embodiments, especially those wherein the nozzle is located in close proximity to rim 108 (e.g. as illustrated in FIG. 5) such vacuum effect can serve to draw tissue within cup 206 so that liquid jet 210 can contact the tissue within the surgical site directly, so as to enable the jet itself to cut and excise tissue. In certain such embodiments, rim 108 of cup 206 need not be sharpened so that it is able to cut tissue. Instead, in such embodiments, the rim and cup can serve only to provide a means for facilitating controlled depth and area cutting by the liquid jet itself. In such embodiments, the liquid jet can serve both to cut and fragment and/or disaggregate the tissue, simultaneously, while also facilitating the removal of the tissue from the operative site through the evacuation lumen. A detailed description of the effect of nozzle positioning in creating a localized vacuum effect tending to draw tissue into a receptacle placed in contact with tissue, and design parameters for creating and controlling such effect, can be found in commonly-owned U.S. Patent Publication No. 2003/0125660.

A significant advantage provided by liquid jet-assisted device 200, as compared to conventional curettes such as device 100, is that the surgeon, after excising a first piece of tissue with the device, need not remove the device from the surgical site to remove this tissue from the curette cup. Instead, as discussed above, the action of the liquid jet can facilitate the removal of the piece of tissue from the surgical site and/or disaggregation of the tissue in situ, so that the surgeon may then excise additional pieces of tissue from the patient with the device in a similar fashion without the necessity for removing the device from the patient. As discussed above, this functionality, provided by the present invention, is especially important for surgical procedures performed in delicate, challenging environments, such as, for example the spine of a patient.

FIGS. 6 and 7 illustrate an alternative embodiment for constructing liquid jet-assisted curette device 200 according to the invention. Because the proximal end can be substantially similar to that illustrated previously in FIG. 2, only a portion of the neck/shaft 204 and distal end is illustrated. In the illustrated embodiment, evacuation lumen 602 and high pressure lumen 604 are separable from, and configured to be contained and immobilized within, a curette cup-providing sleeve component 606. Sleeve component 606 can, in certain embodiments, extend proximally only partially along shaft 204, and not all the way to the handle (not shown). In such embodiments, component 606 can be rigidly attached to the pressure and evacuation lumen, e.g. by welding, brazing, or some other means of rigid attachment. In such embodiments, the support for component 606 is provided by shaft 204. In alternative embodiments, component 606 can extend proximally all the way to the handle (not shown) and be rigidly attached to the handle or have a proximal end comprising part of the handle structure itself. In such embodiments, it may not be necessary for the evacuation lumen and/or the pressure lumen to be rigidly attached to and immobilized with respect to component 606. In fact, in certain such embodiments, as discussed below in the context of FIGS. 10 and 11, one or both lumens may be longitudinally movable with respect to component 606 and/or each other to adjust the position of the nozzle and/or evacuation lumen with respect to component 606.

Component 606 can include, at its distal end, a curette cup 608, which can be similar in shape and size to cup 206. Component 606 can be shaped and configured to include longitudinally oriented channels 610 and 612 therein that have a shape and size complimentary to evacuation lumen 602 and high pressure lumen 604, respectively. Component 606 can be configured to be clamped or be otherwise affixed to the evacuation lumen and high pressure lumen during operation. In operation, a nozzle 614, which can comprise a hole in the side wall of high pressure lumen 604, can be configured and positioned to emit a liquid jet 210 creating an entrainment region 224 that at least partially fills jet receiving opening 616 of evacuation lumen 602, during operation. As described in detail in commonly owned U.S. Pat. No. 6,375,635, such substantial filling of the jet-receiving opening by the entrainment region created by the jet can enhance performance of the device and evacuation of fluid and debris through the evacuation lumen.

As illustrated most clearly in FIG. 7, surgical instrument 200 as configured in FIGS. 6-11 can be constructed by combining two sub-assemblies; sub-assembly 618 comprising a combination of evacuation lumen 602 and high pressure lumen 604, and sub-assembly 620 comprising distal component 606 that includes distally positioned curette cup 608. As mentioned above, depressions 610 and 612 in component 606 are shaped and sized to accommodate the profiles of the evacuation lumen 602 and high pressure lumen 604, when the device is assembled in an operable configuration. In certain embodiments, an operative device can be assembled by sliding, or otherwise inserting, sub-assembly 618 into a proximal opening 622 of assembly 620 then, in certain embodiments, the two sub-assemblies can be affixed together by any suitable means, including, but not limited to, means such as adhesives, braising, welding, clips, detents, shrink wrapping, etc., as would be apparent to those of ordinary skill in the art. In certain embodiments, in order to facilitate positioning and assembly, high pressure lumen 604 of sub-assembly 618 can, optionally, be affixed to evacuation lumen 602, by any of the affixing means recited above, or any others apparent to those of ordinary skill in the art, prior to insertion of sub-assembly 618 into sub-assembly 620. While the above embodiments illustrate some of the many ways of configuring and assembling a liquid jet-assisted curette device provided by the invention, it should be apparent that they are merely exemplary and far from exhaustive of the many possible configurations and techniques for assembling a device within the scope of the present invention.

FIGS. 8 and 9 illustrate another embodiment for configuring a distal end portion of curette 200 utilizing a liquid jet according to the invention. The distal end 800 is substantially similar in construction and design to that previously described in FIGS. 6 and 7. The major differences are that in distal component 801, the peripheral rim of curette cup 803 comprises a plurality of claws 802 or serrations instead of being an essentially continuous sharpened edge, as was the case for rim 108 of curette cup 608. In addition, evacuation lumen 805 includes therein a necked-down region 804, the purpose and function of which are explained in more detail below and in commonly owned, U.S. Pat. No. 6,375,635.

Serrated teeth 802, when utilized for cutting or scraping tissue in a surgical operating field, tend to produce smaller pieces of tissue than a curette having a continuous peripheral rim providing a cutting edge. For certain embodiments, especially when the curette is utilized to scrape or cut hard tissues, such as cartilage and/or bone, reducing the size of pieces of tissue within cup 803 produced by cutting or scraping with the curette can reduce clogging of the evacuation lumen by large chunks of hard tissue or bone not fully fragmented and/or disaggregated by the liquid jet. In addition, when the cutting edges of cup 803 are brought into contact with tissue, the open spaces 806 between teeth 802 can serve, to provide venting to reduce the liquid jet-generated suction effect attending to draw tissue into the tissue receptacle portion 807 of the curette cup (See commonly-owned U.S. Patent Publication No. 2003/0125660 A1 for more detail on venting) and can improve liquid jet-driven evacuation from the device through an evacuation lumen, when provided.

Constriction or pinch 804 of evacuation lumen 805 is able, in certain embodiments, to enhance the degree of fragmentation and/or disaggregation of tissue and debris with the liquid jet, reduce tissue clogging, and to enhance the degree of suction at jet-receiving opening 616 created by passage of the liquid jet and entrainment region through evacuation lumen 805. As explained in more detail in commonly owned U.S. Pat. No. 6,375,635, fragmentation and/or disaggregation can be enhanced by constriction 804 by the provision of a constricting region 808 providing liquid jet contacting surfaces 810 and a region 812, upstream of the constriction, in which turbulent high sheer flow is present. For embodiments such as illustrated in FIGS. 8 and 9 including a constriction 804, the minimum diameter of the constriction at point 814 can be between about 25-99%, and in certain embodiments between about 75-80%, of the internal diameter of the evacuation lumen region 812 upstream of the constriction.

The degree of suction at liquid jet-receiving 616 and the efficiency of liquid jet-driven evacuation can be enhanced by the expansion in diameter occurring from the minimum diameter portion 814 of the constriction to the diameter of the evacuation lumen 805 downstream of the constriction. In certain preferred embodiments, the inner diameter of evacuation lumen 805 downstream of constriction 804 is somewhat larger than the diameter of the evacuation lumen upstream of the constriction. Such expansion in diameter can act as a diffuser enhancing suction as the liquid passes through the evacuation lumen. In other embodiments of the inventive surgical instruments not including a constriction such as 814 providing a downstream expansion, it is preferred, in certain embodiments, to provide somewhere within the evacuation lumen, or the evacuation plumbing downstream of the evacuation lumen, an expansion in diameter providing a diffuser element bringing about the above-described enhanced suction effect. In certain embodiments, such a diffuser may be provided by simply expanding the internal diameter of the evacuation lumen at some point along its length downstream of constriction 814. In another embodiment in which constriction 814 is not present, a diffuser may be effected by, for example, making the jet-receiving opening inner diameter smaller than the inner diameter of the evacuation lumen at any point downstream of the jet-receiving opening. In the above and/or other embodiments, an expansion can be provided by interconnecting the evacuation lumen, for example within handle 202 as illustrated in FIG. 2, to an evacuation tube 230 having a larger internal diameter than the evacuation lumen. An exemplary expansion of the evacuation line provided at an interconnection between the evacuation lumen, for example evacuation lumen 204 of device 200, and an evacuation tube, for example evacuation tube 230, could be provided by interconnecting the exemplary evacuation lumen mentioned previously, having an internal diameter of about 0.118 inch, with evacuation tubing comprising, for example, flexible plastic tubing having an internal diameter ranging between about 0.15 inch and about 0.25 inch.

FIGS. 10 and 11 illustrate yet another alternative embodiment for configuring liquid jet-assisted curette instrument 200, which is substantially similar to the configuration described in the context of FIGS. 8 and 9 above, except that the longitudinal position of evacuation lumen 805 and/or nozzle 614 of high pressure lumen 604 is adjustable with respect to sleeve component 1002 and curette cup 803. As described above, the relative position of the nozzle within the curette cup and the degree of clearance in the curette cup distal to the position of nozzle, in which tissue not subjected to the liquid jet and can accumulate, can affect the performance and tissue removal efficiency of the instrument. In many cases, optimal positioning of the nozzle within the curette cup may vary depending upon the particular type of tissue being excised and the geometry and configuration of the surgical site. In some instances, optimal positioning can change during a particular procedure, such that a desired or optimal position of the nozzle and/or evacuation lumen jet-receiving opening 616 with respect to the distal-most end of the curette cup may change during the procedure.

FIG. 10 illustrates an embodiment wherein sleeve component 1002 including curette cup 803 at its distal end is longitudinally moveable in the direction of arrows 1004, so that the distance 1006, defining the clearance within cup 803 distal of nozzle 614, is adjustable while maintaining a separation distance 1008 defining the liquid jet length. By contrast, in the configuration illustrated in FIG. 11, the position of sleeve component 1002 is fixed with respect to the body/handle of the instrument, and at least one of evacuation lumen 805 and high pressure lumen 604 is moveable with respect to sleeve 1002. Thus, by adjusting the longitudinal position of one or both of evacuation lumen 805 and high pressure lumen 604, an operator of the instrument can adjust one or both of distances 1006 and 1008. In certain embodiments, the configurations illustrated in FIGS. 10 and 11 could include a proximal end including a mechanism for facilitating the control and relative positioning of the longitudinally moveable elements by an operator of the instrument. A wide variety of suitable mechanisms for actuating such longitudinal movement would be readily apparent to those of ordinary skill of the art and could, for example, comprise a mechanism similar to that disclosed below in the context of the inventive rongeur-type instruments (see FIGS. 13 and 14). Additionally, a variety of mechanisms for facilitating longitudinal adjustment of the position of a pressure lumen and/or evacuation lumen of a liquid jet device are described in commonly-owned U.S. Pat. Nos. 5,944,686 and 6, 375,635.

The inventive liquid jet-assisted curettes, in certain embodiments, may be suitable for many of the functions now performed by conventional curettes. One use that is suitable for certain embodiments of the inventive curettes is surgery on the spine of a patient, for example removal of the disc nucleus, or scraping cartilage from bones to stimulate spinal fusion. In addition, certain embodiments can be used more generally for tissue resection and/or removal, particularly of soft tissue. Removal of tumors, necrotic soft tissues, fibroids, cysts, and entire organs or portions thereof can be effected with certain embodiments of the inventive curette devices. In addition, the inventive curette may be configured to provide one or both poles of an electrocautery system, for example as described in more detail in commonly owned U.S. Pat. No. 6,451,017, incorporated herein by reference.

Described below, in the context of several embodiments of fluid jet-assisted rongeur-type instruments, are surgical instruments provided according to the invention that include a user-actuated tissue-manipulating component at their distal ends. As described above, such instruments, as illustrated and described in more detail below, typically include a proximal end having at least a portion thereof configured to be grasped and/or manipulated by an operator. The proximal end, or a portion thereof, is operatively coupled to the tissue-manipulating component of the distal end to facilitate control and actuation of the tissue-manipulating component from a non-manipulating configuration to a manipulating configuration by manipulation of the proximal end of the instrument.

For example, in a rongeur, bone punch, or forceps instrument, the proximal end of the instrument may include a scissors-like handle configuration which, upon squeezing, opens, closes, or otherwise moves a component of the distal end of the instrument to effect tissue cutting, gripping, retracting, etc. As mentioned above, a wide variety of such instruments are known in the art and can potentially be configured for use with a liquid jet, according to the invention, to improve their performance or facilitate new functionality.

In the specific examples below, the embodiment of a Kerrison-style rongeur with a longitudinally-slideable tissue gripping and/or cutting component is illustrated and discussed. The below-illustrated and described instruments including slideable cutting elements for excising tissue, especially hard tissue such as cartilage and bone, are often referred to as rongeur punches or bone punches. While a particular configuration is exemplified in the illustrations below, it should be understood that similar instruments providing similar or identical functionality may have a wide variety of shapes and sizes for use in particular surgical procedures, as well as for different actuation (i.e. opening/closing) schemes. In addition, when such instruments have moveable components, such as moveable jaws, cutters, etc., the instruments may be configured with any of a wide variety of different mechanisms configured to maintain the jaws of the instrument in a normally-open, normally-closed, or partially-opened configuration. In addition, as described in more detail below, these instruments, and indeed any instruments provided according to the invention described herein, may be supplied as part of a kit in which the instruments are entirely or partially disposable.

Unless otherwise noted, the configurations, dimensions, and design considerations that go into designing the various components of the liquid jet assist components of the instruments (e.g. the pressure lumen, nozzle, evacuation lumen, liquid pressures, etc.,) may be similarly configured as those previously described in the context of the curette instruments and/or the instruments described previously in commonly owned U.S. Pat. Nos. 5,944,686; 6,375,635; and 6,511,493; and U.S. Patent Application Nos. 2003/0083681 A1 and 2003/0125660 A1.

FIG. 12 illustrates a conventional surgical instrument 1200 having a rongeur-type handle 1202 including a fixed portion 1204 and a moveable portion 1206 connected by a pin connector 1208 and biased by springs 1210 and 1212 configured to keep jaws 1214, positioned at the distal end of the instrument, normally opened. Stationary handle portion 1204 is connected to a longitudinally- and distally-extending shaft portion 1216 terminating at its distal end in a foot plate 1218 that may have a rounded, blunt distal-most surface 1220 and includes a cavity 1222 therein (dotted lines). Connected to moveable handle portion 1206 is a longitudinally-slideable component 1224. Slideable component 1224 is configured to move longitudinally forward in the direction of arrow 1226, when an operator actuates handle 1202 by squeezing. Upon actuation, the distal edge 1228 of slideable component 1224 moves forward (dotted lines) and terminates, when the jaws are completely closed in cavity 1222. Typically, one or both of distal edge 1228 and edges 1230 of cavity 1222 are sharpened so that, upon closing the jaws, slideable component 1224 is able to snip, punch, or otherwise sever tissue in an operating field. For certain typical rongeurs and punches utilized for spine surgery applications, "bite opening" length 1232 is typically on the order of about 16 millimeters. When using device 1200, a surgeon, after snipping or punching a piece of tissue in the surgical operating field, typically must remove the instrument from the operating field at some point to remove tissue from slideable component of 1224 to prevent fouling or clogging of the instrument.

Figure 13:
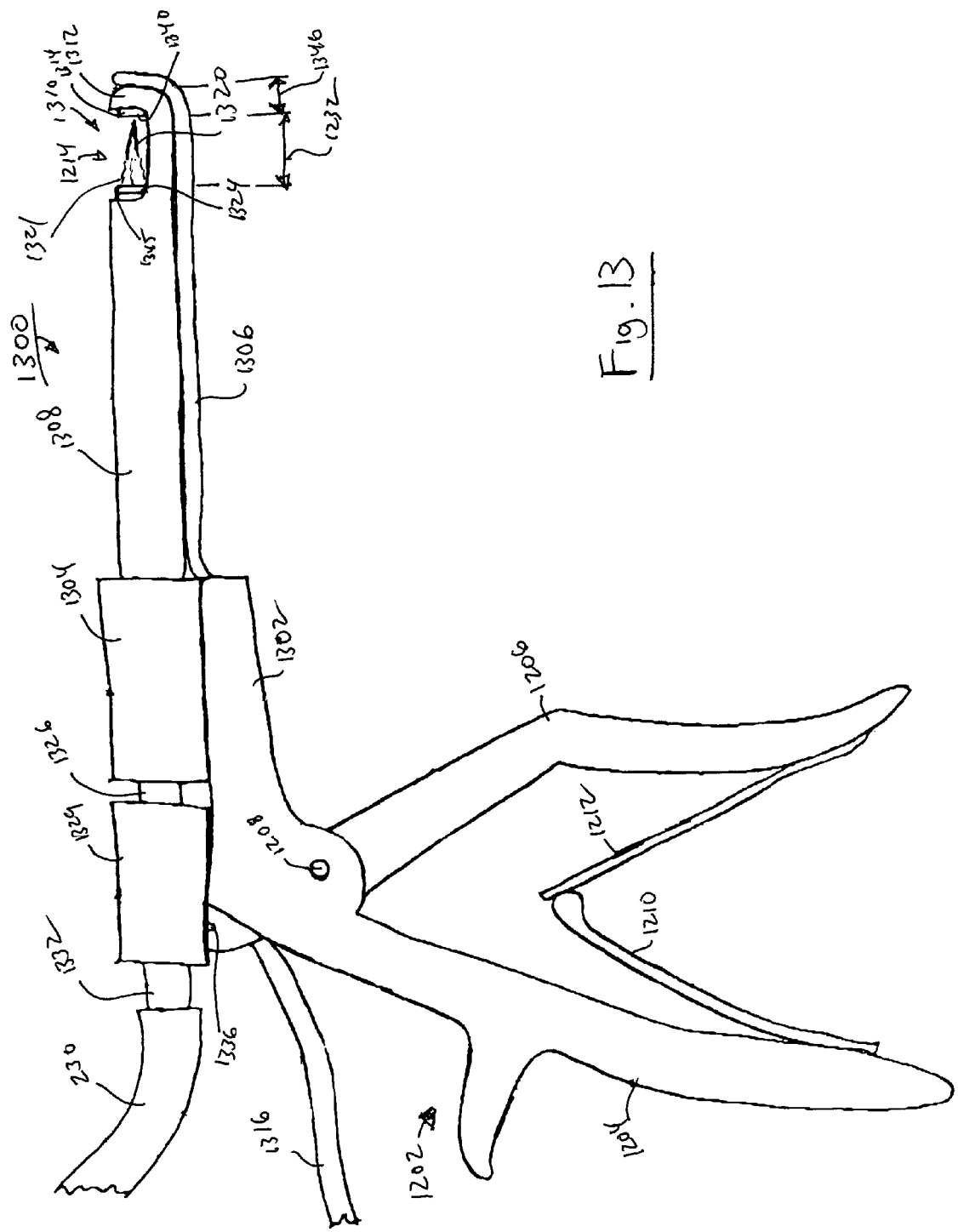
FIG. 13 is a schematic side elevational view of liquid jet-assisted rongeur-type surgical instrument according to one embodiment of the invention.
Figure 14:
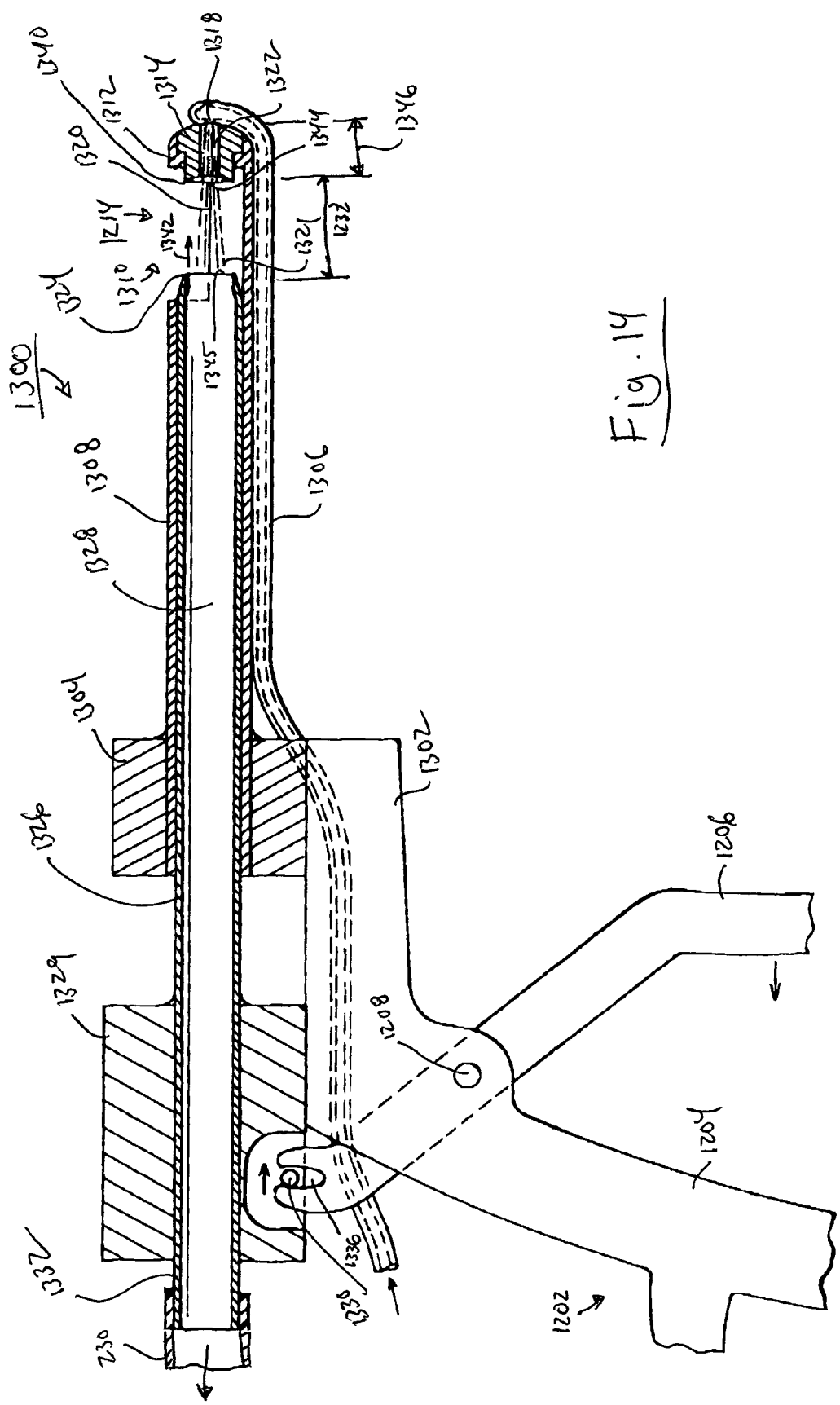
FIG. 14 is a partially broken away fragmentary view of the liquid jet-assisted rongeur-type surgical instrument illustrated in FIG. 13.

One embodiment of an inventive rongeur-type instrument providing a liquid jet-forming nozzle at a distal end thereof configured to contact tissue excised with the instrument in a surgical operating field is illustrated in FIGS. 13 (external view) and 14 (partially cut-away view). Liquid-assisted rongeur 1300 comprises one embodiment of a fluid jet-enhanced version of conventional rongeur instrument 1200 shown in FIG. 12.

Surgical instrument 1300, similar to conventional instrument 1200, can comprise a rongeur-type handle 1202 that can have a fixed portion 1204 and moveable portion 1206 connected by a pin connector 1208 and separated by biasing springs 1210 and 1212, which, in the illustrated embodiment are configured to maintain jaws 1214 in a normally-open configuration. A distal extension 1302 of the fixed handle portion 1204 can be configured to support a fixed housing component 1304, which can be affixed thereto. Distal extension 1302 can also provide support for a high pressure lumen 1306, which may extend distally from distal extension 1302 to the distal end of the instrument. Fixed housing component 1304 can be connected to and support distally extending sheath 1308. Distally extending sheath 1308 may include a notch 1310 therein at its distal end defining the "bite opening" of jaws 1214. Distally extending sheath 1308 may also include at its distal most end, distal to notch 1310, an annular ring portion 1312 having a shape configured to mate with, support, and be rigidly attached to a cutting and/or gripping head component 1314, the structure and function of which is explained in more detail below.

At the proximal end of the instrument, a high pressure hose 220 can connect to fixed handle portion 1204 and to high pressure lumen 1306. Alternatively, high-pressure hose 220 may be connected to high pressure lumen 1306 and supported by distal extension 1302 of handle portion 1204 without being directly connected to the handle. High pressure lumen 1306 includes a liquid jet-forming nozzle 1318 at its distal end (FIG. 14), which is configured to form a liquid jet 1320 creating an entrainment zone 1321 (dashed lines) directed across notch 1310. Cutting/gripping head component 1314 may include a jet passage 1322 therethrough (FIG. 14), which permits liquid jet 1320 to pass through the cutting/gripping head and into notch 1310 during operation.

Surgical instrument 1300 can further comprise a longitudinally slideable plunger cutting/gripping head 1324 comprising a distal end of longitudinally slideable plunger 1326, which can, optionally, be sharpened to provide a cutting edge. As illustrated, and optionally, plunger 1326 can be hollow along its entire length, thereby providing an evacuation lumen 1328 for removal of tissue and debris from a surgical site, as explained in more detail below. In other embodiments, the plunger may comprise a solid rod having a hollow portion only near its distal end for forming the distal cutting/gripping head, or may have a proximal end that is plugged to prevent fluid flow through the tube. In addition, while plunger cutting/gripping head 1324 and distal cutting/gripping head component 1314 can be provided with sharpened edges, providing tissue-cutting components, in alternative embodiments, these components may be unsharpened so that the jaws 1214 act not as to punch or cut with sharpened blades, as illustrated, but rather as a clamp, forceps, grabber, or retractor. In certain such embodiments, the liquid jet acts to cut and/or excise the tissue immobilized by the jaws 1214. In addition, for embodiments of plunger 1326 providing an evacuation lumen 1328, the distal end of plunger 1326 may also include a constriction therein (e.g. similar to necked-down region 804 illustrated in FIG. 8) configured to enhance evacuation and/or disaggregation of tissue by the jet during operation.

Plunger 1326 may be attached to and carried by moveable housing component 1329, which, in turn, may be connected to the moveable handle portion 1206 of handle 1202 via connecting pin 1330. In the illustrated embodiment, hollow plunger 1326 provides an evacuation lumen 1328 and is connected at its proximal end 1332 to an evacuation waste hose 230. In operation, pulling handle portion 1206 proximally towards fixed handled portion 1204 moves slot 1336 at the top of handle portion 1206 distally, which, in turn, drives pin 1330 distally, thereby moving moveable housing component 1329, plunger 1326, and plunger cutting/gripping head 1324 longitudinally forwardly toward fixed cutting/gripping head component head 1314. It should be appreciated that in other embodiments, the particular opening and closing mechanism illustrated may be substituted with a variety of other actuating mechanisms. For example, instead of having plunger 1326 longitudinally movable upon actuation of the handle, in an alternative embodiment, the plunger could remain stationary while distally extending sheath 1308 and cutting/gripping head component 1314 move proximally. In yet another embodiment, upon actuation of the handle, the plunger 1326 could be configured to move distally while, at the same time, sheath 1308 and cutting/gripping head 1314 move proximally.

The fully-open space between plunger cutting/gripping head 1324 and the proximal edge 1340 of fixed cutting/gripping head 1314 forms jaws 1214 and defines bite opening length 1232. In operation, tissue to be cut can be positioned within jaws 1214, and handle 1202 can be actuated by an operator to drive plunger cutting/gripping head 1324 forward in the direction of arrow 1342 and into the tissue (not shown) in notch 1310. The diameter of the periphery of edge 1340 of fixed cutting/gripping head 1314 can be selected to be very slightly smaller than the inner diameter of plunger cutting/gripping head 1324. Upon bringing plunger cutting/gripping head 1324 together with peripheral edge 1340, when these edges are sharpened to provide cutting blades, a plug of tissue being cut by plunger cutting head 1324 will be severed and contained within the distal end of evacuation lumen 1328, which comprises a conduit-shaped tissue receptacle. Plunger cutting/gripping head 1324 and fixed cutting/gripping head 1314 may, preferably, be constructed from durable, hardened, surgically acceptable materials, for example hardened stainless steel, and sized so that a plug of tissue cut by the combination will have a diameter less than that of the minimum inner diameter of any evacuation lumen provided in the instrument. The optional shallow cavity 1344 recessed into the proximally-oriented face of fixed cutting head 1314 comprises a flair which can advantageously prevent bone chips from becoming lodged in passage 1322 of the cutting/gripping head during operation.

With a conventional rongeur instrument, such as instrument 1200 illustrated in FIG. 12, after taking one or a few "bites" of tissue, it would usually be necessary to withdraw the rongeur to remove the cut tissue plugs. By contrast, when utilizing inventive surgical instrument 1300, high pressure liquid, such as isotonic saline, can be supplied to nozzle orifice 1318 to form high pressure liquid jet 1320 during and/or after taking a "bite" of tissue with the instrument. Liquid jet 1320 can be positioned to impact tissue excised by the cutting/gripping heads and cut, fragment and/or disaggregate, and flush or push the tissue proximally through evacuation lumen 1328 and away from the surgical site, thereby removing the tissue from the surgical site without the need to remove the entire instrument from the surgical site. As discussed above in the context of the inventive curette-type devices providing tissue and fluid evacuation, in certain embodiments, evacuation lumen 1328 can be connected in fluid communication with a source of external suction, such as a vacuum pump, to bring about or enhance evacuation of fluid and material with the device. In other embodiments, the liquid jet and evacuation components can be configured, as previously described and as described in commonly-owned U.S. Pat. No. 6,375,635, to enable the force created by the liquid jet to evacuate fluid and debris away from the surgical site without the need for use of an external source of suction.

In one embodiment of a method for using inventive surgical instrument 1300 for cutting and removing tissue, the surgeon can first excise a piece of tissue by actuating handle 1202 to drive an (optionally) sharpened plunger cutting/gripping head 1324 distally to excise a plug of tissue. After excising the tissue, the surgeon can then continue to squeeze handle 1202 to maintain the jaw in a closed configuration. Then, while maintaining the jaw in a closed configuration, the surgeon can turn on the liquid jet so that the liquid jet can fragment and/or disaggregate and erode at least a portion of the tissue plug (which would now be inside lumen 1328 of plunger 1326), and/or force the debris proximally through lumen 1328 with the liquid jet. After removal of the tissue plug, the surgeon could turn off the jet, allow jaws 1214 to open once again, take the next "bite" of tissue, and repeat the above-described process. In such an embodiment, the maximum length of the liquid jet during operation (i.e. the distance between the outlet of jet nozzle 1318 and the jet-receiving opening 1345 of the plunger cutting/gripping component 1324 comprises a distance 1346 essentially equal to the length of fixed cutting/gripping head 1314. To minimize dispersion of the jet, this length can be selected to be within the order of a few millimeters (e.g. between 2-5 millimeters).

In a similar embodiment, except using a surgical instrument 1300 in which cutting/gripping component 1324 and fixed cutting/gripping head 1314 are not sharpened to provide cutting edges, the surgeon can first grasp a piece of tissue in jaws 1214 by actuating handle 1202 to drive an unsharpened plunger cutting/gripping head 1324 distally to grasp and immobilize a piece of tissue. After grasping and immobilizing the tissue, the surgeon can then continue to squeeze handle 1202 to maintain the jaw in a closed configuration. Then, while maintaining the jaw in a closed configuration, the surgeon can turn on the liquid jet so that the liquid jet can cut and excise the piece of tissue from the patient and fragment and/or disaggregate and erode at least a portion of the tissue piece, and/or force the tissue debris proximally through lumen 1328 with the liquid jet. After removal of the tissue piece, the surgeon could turn off the jet, allow jaws 1214 to open once again, grab the next piece of tissue, and repeat the above-described process.

In certain embodiments, it may be desirable to configure the instrument so that either the liquid jet is continuously on during operation, or the instrument is configured to provide flexibility enabling an operator to cut and/or excise, fragment and/or disaggregate, and evacuate tissue and debris with the liquid jet both when the jaws of the instrument are fully open, as well as partially or fully closed. As discussed previously, in certain rongeur instruments utilized for spinal surgery, bite distance 1232 can be as much as about 16 millimeters. In such embodiments, wherein it is desirable to utilize the liquid jet with the jaws open as well as closed, in order to prevent an undue level of dispersion of liquid jet 1320 causing the entrainment zone 1321 to become larger than the diameter of the jet-receiving opening 1345 of the distal end of plunger cutting/gripping head 1324 (resulting in undesirable "blow by" of the fluid jet and a reduction of visibility and effectiveness of evacuation), it can be desirable to configure the jet-forming elements of the instrument to create a highly coherent liquid jet, for example, a jet characterized by a dispersion angle (defined as an apex angle of a cone-shaped region that circumscribes and contains the jet along its length and has an apex at the jet-forming opening of the nozzle and a base defined as the cross-sectional area of the dispersed jet measured in a plane co-planar to the cross-sectional plane through the evacuation lumen at its point of minimum diameter) of between about 3-10 degrees, an in certain embodiments, between about 3-6 degrees.

Techniques for forming nozzles able to create such coherent liquid jets are described in commonly-owned U.S. Pat. No. 6,375,635. In certain embodiments, it is desirable in forming coherent jets to provide a nozzle having a ratio of nozzle length to jet opening diameter of at least about four, in certain other embodiments of at least about six, and in yet other embodiments of at least about ten. In addition, as described in U.S. Pat. No. 6,375,635, the efficiency of a nozzle and its ability to form a highly coherent jet is improved by forming the nozzle to provide a smooth, tapering flow path for the liquid flowing into the nozzle, thus reducing turbulence, recirculating flow patterns, and friction at the jet nozzle inlet. This effect is known in the fluid mechanical arts as the "vena contracta" effect and can improve fluid flow efficiencies by as much as 30% or more. Techniques for forming tapered nozzles having a large ratio of length to minimum diameter and capable of forming highly coherent liquid jets (e.g. by necking down the end of a length of high pressure tubing) are described in detail in the above-referenced U.S. Pat. No. 6,375,635. Such nozzles could be utilized for forming the liquid jet nozzle of surgical instrument 1300.

In one particular embodiment for creating a highly coherent liquid jet, e.g. with a cone apex angle less than 10 degrees and, in some embodiments between about 3-6 degrees, in surgical instrument 1300 (or in any other of the liquid jet surgical instruments of the invention, for example curette 200) the nozzle can be formed and configured as described in commonly owned, co-pending U.S. Patent Application Ser. No. 60/444,344 to Kevin P. Staid and James J. Frassica; titled "Improved Nozzle for High Pressure Liquid Jet" and filed Jan. 31, 2003, which is incorporated herein by reference. Such a nozzle is comprised of a pre-fabricated nozzle ring 1500 as illustrated in FIG. 15 having a flat distal-facing surface 1502 and a hemispherical, proximal facing surface 1504. As illustrated in FIG. 15, in certain embodiments, the cross-sectional shape of the ring-shape nozzle insert 1500 comprises a half circle having a radius R. Centrally located annular aperture 1506 comprises the jet opening of the annular nozzle insert 1500.

As described in U.S. Patent Application Ser. No. 60/444,344, nozzle ring insert 1500 can have a toroidal topology with a central passage 1506 that defines the diameter of the fluid jet emitted from it. Any suitable technique may be used to make the nozzle rings. Preferred techniques will provide very smooth surfaces for proximally-facing portion 1504 of the insert.

In one preferred technique, the inserts can be fabricated utilizing a photolithographic technique coupled with subsequent electrodeposition. Alternatively, nozzle ring 1500 could be made by drilling holes in pre-formed blanks, by mechanical drilling, laser drilling, electric discharge machining, or any other known technique capable of reliably making holes with a desired diameter. In one exemplary embodiment, a laser is used to cut both the central hole 1506 defining the nozzle opening as well as an outer circle 1508 defining the outer diameter of the nozzle ring. These techniques and others are described in greater detail in U.S. Patent Application Ser. No. 60/444,344. Nozzle ring 1500 can then be fabricated into a functioning nozzle by inserting it into a opening in a distal end 1510 or a side wall 1511 of a pressure lumen 1512, and affixing it therein as illustrated schematically in FIGS. 16 and 17, respectively.

For certain embodiments of surgical instruments utilizing nozzles producing highly coherent liquid jets, e.g. those producing a liquid jet having a cone apex angle less than 10 degrees and, in some embodiments between about 3-6 degrees (such as certain of those nozzles configured as illustrated in FIGS. 16 and 17 and described immediately above), an evacuation lumen can be configured to have a somewhat design and internal diameter sizing than previously described. Specifically, in such embodiments, when providing an evacuation lumen having a smallest internal diameter at the location of the jet-receiving opening, jet-receiving opening can be sized so that it has a diameter of between about 150%-300% the diameter of a cross-section of the base of the dispersed jet as it crosses the plane defining the jet-receiving opening. In other of such embodiments, in which an evacuation lumen having a smallest internal diameter at a location of a necked-down constriction at the distal end of the evacuation lumen (e.g. as illustrated in FIGS. 8 and 9) is provided, the jet-receiving opening can be sized so that it has a diameter between about 150%-400% the diameter of a cross-section of the base of the dispersed jet as it crosses the plane defining the jet-receiving opening, and the minimum opening of the constriction can be sized so that it has a diameter of between about 100%-200% the diameter of a cross-section of the base of the dispersed jet as it crosses the plane defining the minimum opening of the constriction.

It should be appreciated and apparent from the description of surgical instrument 1300 that a wide variety of modifications and changes to the physical configuration of the instrument are possible while maintaining its basic principles of operation and the inventive advantages provided by incorporation of a liquid jet. For example, the handle configuration, sheath and barrel length and other dimensions and configurations can vary, depending upon the particular application and surgical arena in which the instrument is employed. In addition, as would be apparent to those skilled in the art, surgical instrument 1300 may utilize many alternative means to activate the tissue-manipulating components at its distal end and may utilize a variety of different types of tissue-manipulating components other than the tissue cutter specifically illustrated. As just one example of an alternative configuration, not illustrated, surgical instrument 1300 could be configured such that the fluid jet nozzle 1318 is located within the distal end of plunger 1326 and positioned so that the liquid jet emitted therefrom is directed distally toward plunger cutting/gripping head 1324 and fixed cutting/gripping head 1314. In such a configuration, the liquid jet could be used to fragment and/or disaggregate and erode pieces of tissue from their proximal side rather than their distal side. In such a configuration, plunger cutting/gripping head 1324 is, optionally, not required to be sharp enough to actually cut tissue, but could rather serve to immobilize tissue being cut by the liquid jet and to contain spray created by the jet.

In another alternative embodiment (not illustrated), to reduce the chance of large bone fragments formed by the device from clogging an evacuation lumen, the distal end of the device could include a supplemental bone plug crushing, grinding, and/or disaggregating component to reduce the size of bone plugs formed by the instrument before such plugs enter the evacuation ilumen. One configuration for providing one such bone/tissue grinding element is described below in the context og FIGS. 18-20. In tone alternative embodiment, the grinding element illustrated in FIGS. 18-20 could be combined with one or more of the tissue excising components at the distal end of instrument 1300, e.g. liquid jet nozzle 1318.

Figure 18:
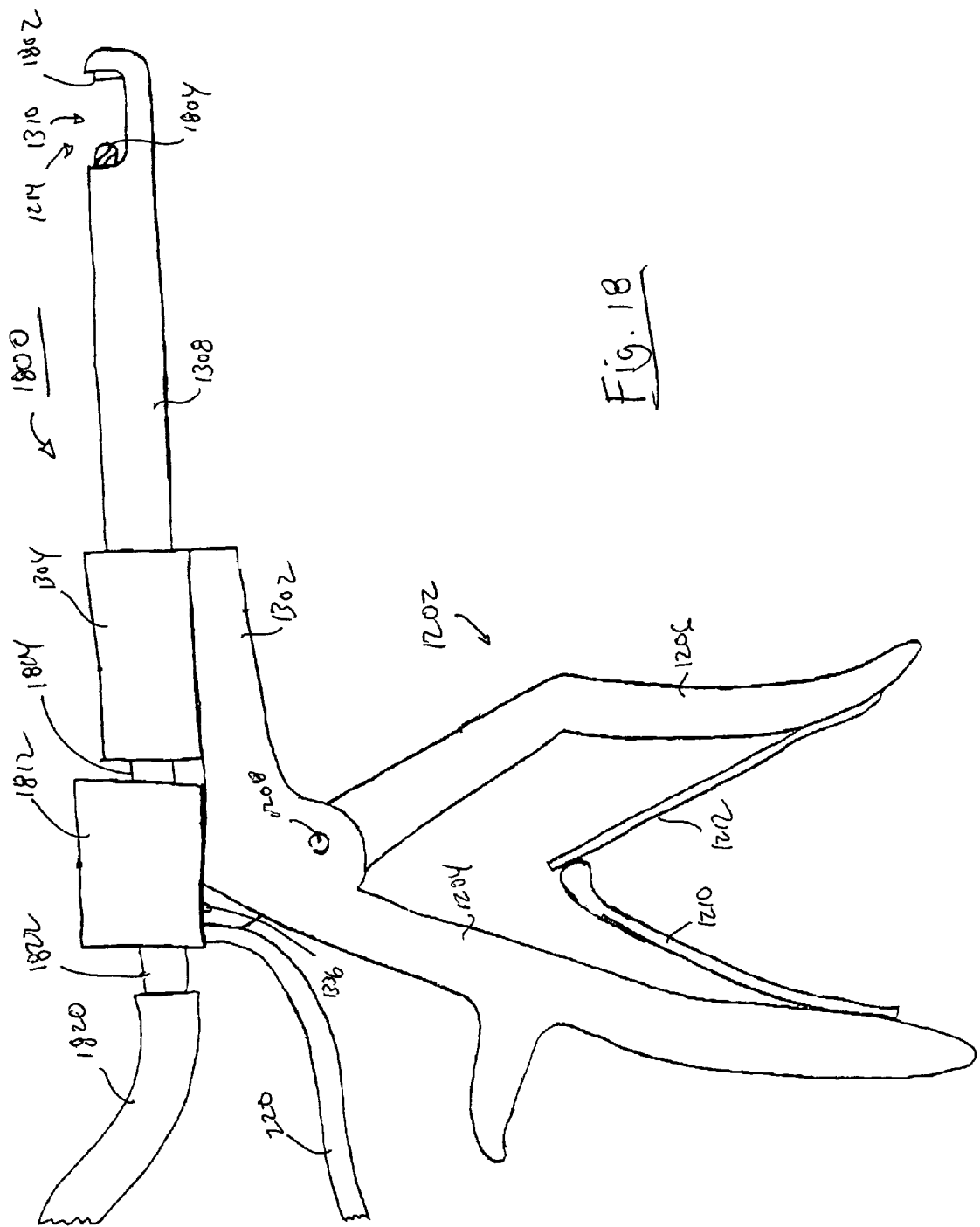
FIG. 18 is a schematic side elevational view of liquid jet-assisted rongeur-type surgical instrument according to another embodiment of the invention.
Figure 19:
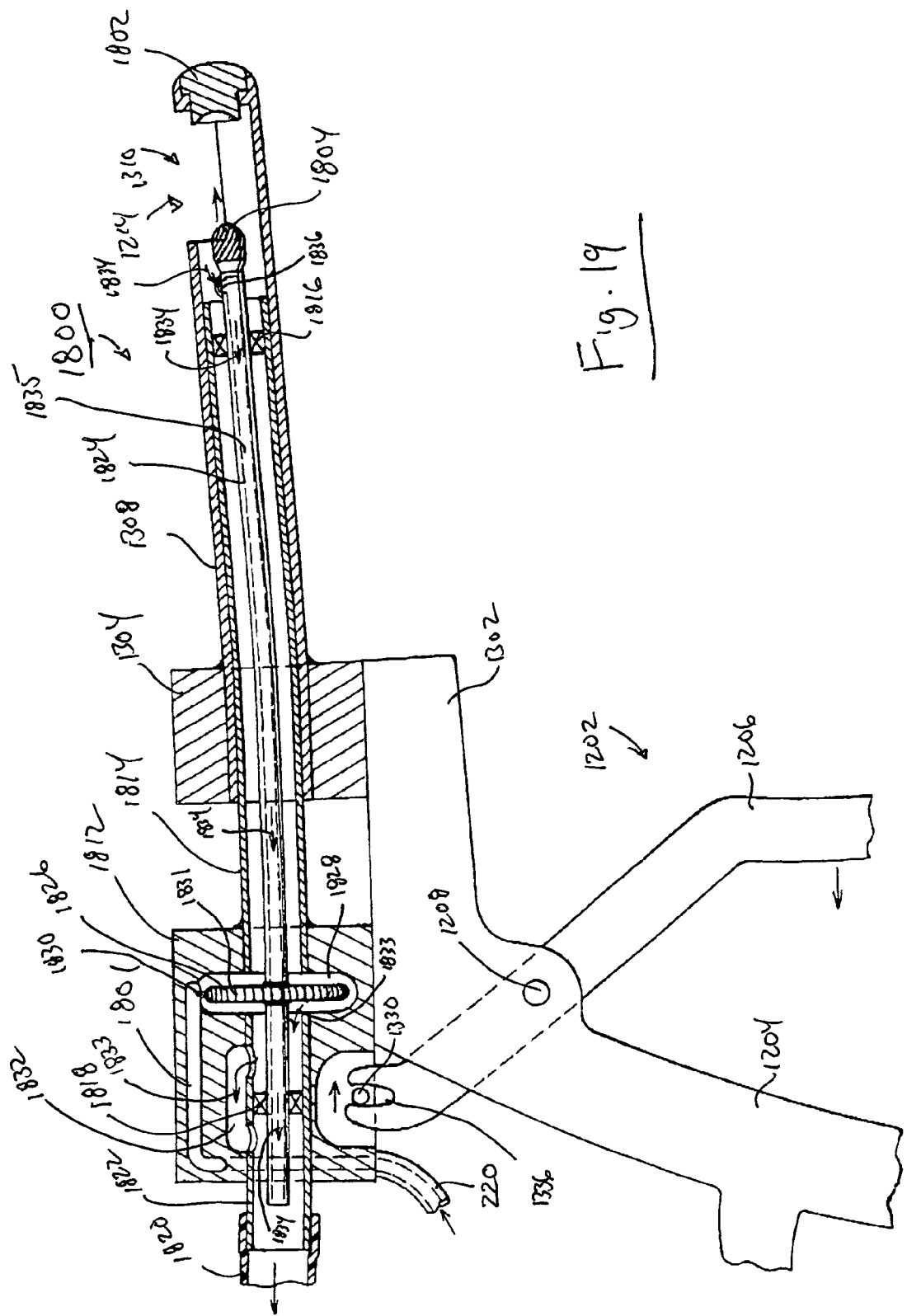
FIG. 19 is a partially broken away fragmentary view of the liquid jet-assisted rongeur-type surgical instrument illustrated in FIG. 18.
Figure 20:
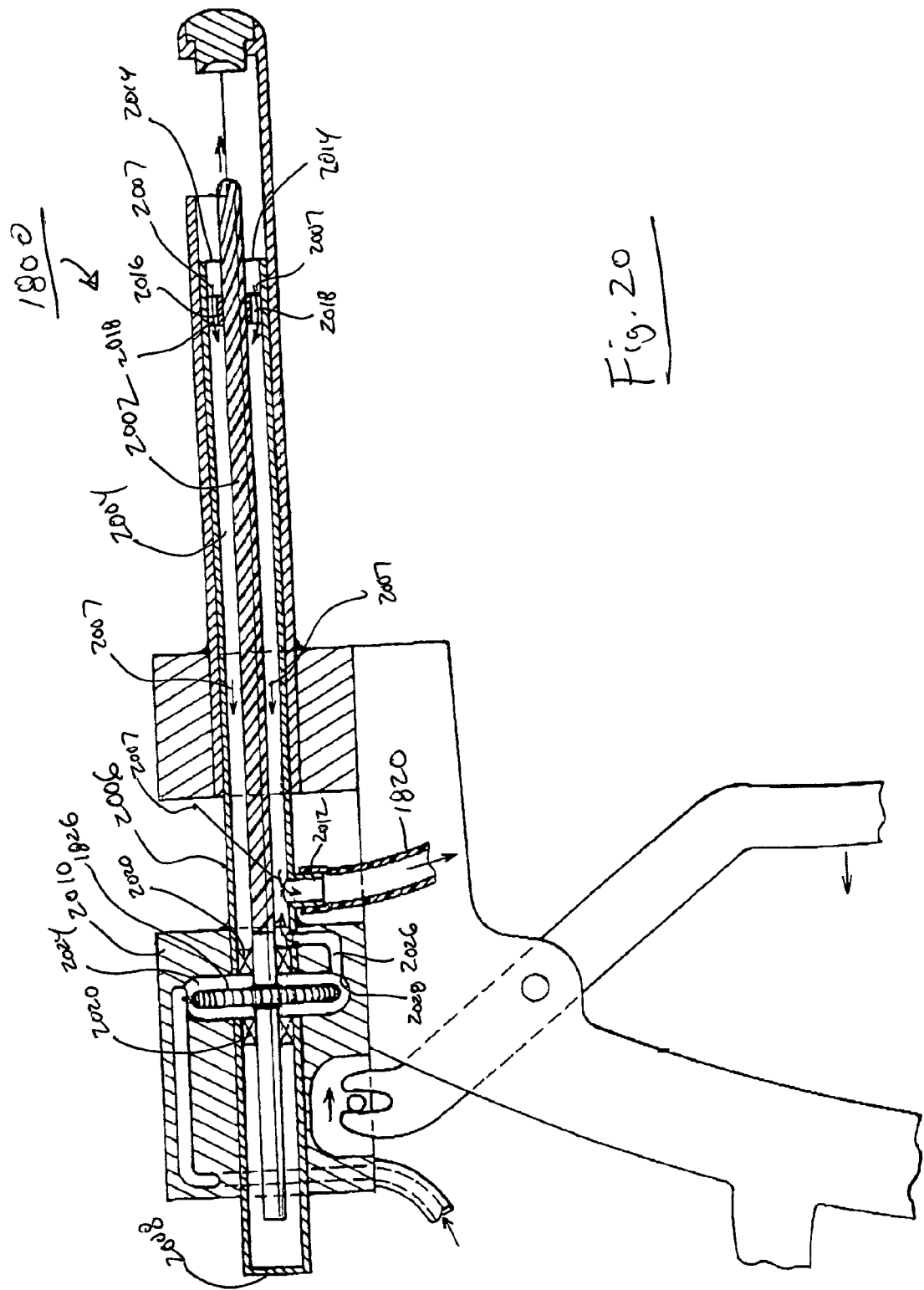
FIG. 20 is a partially broken away fragmentary view of a liquid jet-assisted rongeur-type surgical instrument similar to that illustrated in FIG. 18, except having an alternative configuration for providing evacuation to a surgical site and liquid jet-driven rotor housing chamber.

FIGS. 18-20 illustrate another set of embodiments of a rongeur-type instrument utilizing a liquid jet to bring about fragmentation and/or disaggregation and/or cutting of tissue within a surgical operating field. In contrast to instrument 1300 illustrated in FIGS. 13 and 14, surgical instrument 1800 illustrated in FIGS. 18-20 does not utilize a liquid jet to fragment and/or disaggregate and/or cut tissue by directly impacting tissue with the jet, but rather uses a liquid jet to drive a liquid jet-driven rotor of the instrument, which, in turn, is coupled to a rotatable tissue-contacting component located at the distal end, such that rotation of the liquid jet-driven rotor causes rotation of the rotatable tissue-contacting component. While, in the illustrated embodiments, the rotatable tissue-contacting component comprises a grinding burr, it should be understood, that in other embodiments, the rotatable tissue-contacting component could comprise any one of the wide variety of other useful rotating implements.

Surgical instrument 1800 comprises a liquid jet-driven rotor-powered mechanical cutting tip located at the distal end of the instrument. As with surgical instrument 1300 described previously, surgical instrument 1800 has the general form of the rongeur or punch. In other embodiments, the surgical instrument could be configured in the form of a surgical forceps, morcellator, curette, etc. A "liquid jet-driven rotor" as used herein refers to a liquid jet-driven motor comprising a jet-driven rotor mechanism utilizing a pressure lumen, having a liquid jet forming nozzle therein, which is configured to direct a liquid jet so that it impacts an impacting surface of a rotor, thus driving rotation of the rotor. In the context of a "liquid jet-driven rotor" based motor, the term "liquid" does not encompass gases, as this term was previously defined for use in other contexts.

Unlike typical prior art air or liquid driven turbine mechanisms, a liquid jet-driven rotor mechanism as used herein does not utilize an expanding gas or, as is the case with typical prior art liquid-turbines, confine the rotor and liquid flow path within an enclosed duct or channel such that the rotor is essentially completely submerged in a liquid during rotation. In such typical prior art "reaction" turbines, the liquid driving the rotor undergoes a gradual change in hydrostatic pressure while in contact with the driving surface of the rotor. In contrast a liquid jet-driven rotor mechanism as used herein maintains the liquid jet-driven rotor within a surrounding gas environment while it is being rotatably driven by a liquid jet during operation. Such liquid jet-driven rotor mechanisms as utilized in the context in present invention are described in detail in commonly owned U.S. Pat. No. 6,511,493, which is incorporated herein by reference. The reader is referred to this patent for a description of particular design parameters and configurations for constructing a liquid jet-driven motor. In certain embodiments of the present invention, essentially any of the liquid jet-driven rotor mechanisms described in U.S. Pat. No. 6,511,493 could potentially be utilized in the inventive instruments including such motors. In the illustrations below, one particular configuration that is utilized comprises a liquid jet-driven rotor that is directly attached to a rotating shaft of the instrument carrying the rotatable tissue-contacting component at a distal end thereof such that the rotating shaft and the rotating rotor rotate at the same rotational speed. This particular configuration is described in the above-referenced U.S. Pat. No. 6,511,493, and is also described, illustrated, and discussed in commonly owned U.S. Patent Application Publication Number 2003/0083681 A1.

Referring to FIG. 18, which presents an illustration of the exterior appearance of surgical instrument 1800, and FIG. 19, which shows a first configuration of surgical instrument 1800 in cross section, instrument 1800 includes a rongeur-type handle 1202, having a fixed portion 1204 and a movable portion 1206 pivotally connected by pin connector 1208 and biased in an open position by springs 1210 and 1212. A distal extension portion 1302 of fixed handle portion 1204 is affixed to and supports a fixed housing component 1304, which is attached to and supports distally extending sheath 1308, in a similar fashion as previously described in the context of surgical instrument 1300. Distally extending sheath 1308 is connected to and supports at its distal end fixed burr stop component 1802, which serves a somewhat similar function as fixed cutting head 1314 of surgical instrument 1300 previously described. At the proximal side of notch 1310, and comprising the proximal side of jaws 1214, is the distal end of rotating burr 1804.

At the proximal end of the instrument, a high pressure hose 220 is connected to and supplies high pressure liquid to high pressure lumen 1801 contained within the moveable rotor housing 1812. Burr sheath 1814 is connected to and carried by moveable rotor housing component 1812. Upon actuation of the handle, moveable rotor housing component 1812 moves distally and burr sheath 1814 slides longitudinally and distally within distally extending sheath 1308. Burr 1804 is supported within burr sheath 1814 by distal bearing 1816 and proximal bearing 1818. Burr sheath 1814, as previously mentioned, is attached to and carried by a moveable rotor housing 1812, which is connected to moveable handle portion 1206 via slot 1336 and pin 1330. The waste hose 1820 is connected to the proximal end of burr sheath 1814 via tubing connector 1822. Burr 1804 is connected to the distal end of a burr shaft 1824, which is rigidly attached to liquid jet-driven rotor 1826 located within rotor chamber 1828 of moveable rotor housing 1812. Liquid jet-driven rotor 1826 is driven in rotation via impact with a liquid jet emitted from nozzle 1830 in high pressure lumen 1801. Preferably, as discussed in commonly-owned U.S. Pat. No. 6,511,493, the nozzle is configured to produced a highly collimated liquid jet. Because liquid jet-driven rotor 1826 is directly connected to burr shaft 1824, burr 1804 will rotate at the same speed as rotor 1826, when the instrument is in operation.

In operation, tissue or bone to be cut or abated is introduced into jaw 1214 and handle 1202 is squeezed, which advances moveable rotor housing 1812 distally, and with it burr sheath 1814, burr shaft 1824, and burr 1804. Upon actuation of the handle, burr sheath 1814 slides through distally extending sheath 1308, so that burr 1804 enters into notch 1310. Pressurized fluid is directed through high pressure lumen 1801 to nozzle 1830 to create a liquid jet directed to impact jet-impacting surfaces 1831 on liquid jet-driven rotor 1826. The high pressure liquid jet can accelerate and drive burr 1804 in rapid rotation, for example in the range of about 10,000 RPM to over 50,000 RPM under no-load conditions. Further squeezing of handle 1202 forces the rotating burr 1804 into contact with tissue within notch 1310 of jaw 1214, thereby grinding and disaggregating the tissue.

In an alternative arrangement, not illustrated, burr sheath 1814 may extend distally to a greater extent than illustrated, such that its distal-most portion is distal to or at the same location as the distal most end of burr 1804. In such an alternative configuration, the distal end of burr sheath 1814 could be sharpened to provide a cutting blade/punch similar to plunger cutting head 1324 of instrument 1300 illustrated in FIGS. 13 and 14 and described previously. In such an arrangement, the distal cutting edge of burr sheath 1814 could be utilized to cut target tissue which could then be disaggregated by the action of burr 1804. In another alternative embodiment (not illustrated), a sheath may be provided so that as the burr is moved out of the sheath 1308, the burr sheath 1814 is also extended such that it surrounds the burr and protects contiguous tissue from adventitious contact with the burr 1804 or its shaft 1824.

Referring specifically now to FIG. 19, after the liquid jet impacts rotor 1826, the jet liquid that collects in rotor chamber 1828 is evacuated from the chamber as shown by arrows 1833 via waste tube 1820. In certain embodiments, a source of external suction is applied to waste tube 1820 to effect evacuation of liquid from the device. Moveable rotor housing component 1812 may include a liquid bypass line 1832 therein, as illustrated, which can enable liquid evacuated from rotor chamber 1828 to bypass proximal bearing 1818.

In certain embodiments, as illustrated, liquid and tissue debris can be evacuated from the distal end of the instrument via passage through a lumen 1835 centrally located along the length of hollow burr shaft 1824, which is fluid communication with suction tube 1820 (see arrows 1834). A suction inlet 1836 is provided near the distal end of burr shaft 1824 to enable liquid entry into lumen 1835 in shaft 1824. In certain embodiments, as illustrated, the evacuation opening 1836 can be scooped-shaped and configured so that inlet opening 1836 faces the direction of the burr shaft rotation when in operation. Such a configuration allows for the rotational energy of the burr to assist in or facilitate evacuation of liquid and debris proximally through the lumen 1835 of the hollow burr shaft 1824. Hollow shafted burrs are commercially available (e.g. from Smith & Nephew Dionics) and are described in greater detail in U.S. Pat. No. 6,511,493.

Illustrated in FIG. 20, in cross section, is an alternative embodiment for configuring the evacuation system of liquid jet-driven rotating burr rongeur instrument 1800. In the alternative configuration illustrated in FIG. 20, rotating burr shaft 2002 is solid and does not include an evacuation lumen therein. Rather, liquid and tissue debris at the distal end of the instrument is evacuated through the annular space 2004 surrounding burr shaft 2002 and within burr sheath 2006 (see arrows 2007). Burr sheath 2006 is sealed in its proximal end 2008 and includes, such as at a location proximal to moveable rotor housing component 2010, a suction hose connector 2012, which is in fluid communication with annular space 2004. Upon application of suction to evacuation tube 1820, for example via a source of external suction such as a vacuum pump, tissue and debris can be evacuated from the distal end of burr sheath 2006 through annular inlet opening 2014, through burr shafts spacer element 2016 via passage ways 2018 therein, through annular lumen 2004, and into suction tube 1820 via connector 2012.

In the illustrated configuration of FIG. 20, bearing support for burr shaft 2002 is provided by two proximally-located bearings 2020. Distally located spacer 2016 serves only to prevent burr shaft 2002 from contacting the inner surface of burr sheath 2006 upon lateral deflection, but, in certain embodiments, does not provide any substantial bearing support during normal operation. In fact, in certain embodiments, distal spacer 2016 can be eliminated entirely. A detailed description of various configurations and design considerations for constructing liquid jet-driven burr instruments having only proximally-located bearing support, such as in the configuration illustrated in FIG. 20, is provided in commonly owned U.S. Patent Application Number 2003/0083681 A1, to which the reader is referred for more detail.

Additionally, in the configuration illustrated in FIG. 20, liquid jet rotor housing chamber 2024 is evacuated, so as to remove liquid comprising the liquid jet utilized to drive the rotor in order to maintain the housing free of liquid build-up during operation, via evacuation line 2026, which is fluid communication with suction tube 1820 and enters rotor chamber 2024 at its bottom-most portion 2028. Such a configuration can facilitate removal of liquid within rotor housing chamber 2024 before it collects in a sufficient amount to contact or submerge any part of liquid jet-driven rotor 1826.

In addition to the above-described inventive surgical instruments and methods for performing surgery with such instruments, the present invention also provides a series of kits including one or more of the surgical instruments disclosed herein, or components thereof, together with instructions for use directed to an operator of the instruments. "Instructions" typically involve written instructions on or associated with packaging of instruments, or components thereof, of the invention. Instructions also can include any oral or electronic instructions provided in any manner. The inventive "kits" typically define a package including both any one or a combination of one or more surgical instruments, or components thereof, of the invention and the instructions, but can also include a surgical instrument of the invention, or component thereof, and instructions of any form that are provided in connection with the instrument in any manner such that a professional operator of the instrument will clearly recognize that the instructions are to be associated with the specific instrument.

One embodiment of a kit provided according the invention comprises a surgical instrument of the invention, or a component thereof, in combination with instructions directing an operator to dispose of at least a portion of the instrument after a single use. In certain such embodiments, the instructions direct the operator to dispose of only a portion of the instrument after a single use and to reuse the remainder of the instrument. In particular embodiments, wherein the instructions direct a user to dispose of only a portion of the instrument, the instructions further direct an operator to dispose of one or more of the pressure lumen, evacuation lumen, nozzle, or non-liquid jet tissue-cutting component (e.g. cutting blade, burr, etc.) of the instrument, while retaining the remainder of the instrument for re-use. In another of a series of embodiments, the inventive kits provide instructions directing an operator to dispose of the entire instrument after a single use.

While several embodiments of the invention have been described and illustrated herein, those of ordinary skill in the art will readily envision a variety of other means and structures for performing the functions and/or obtaining the results or advantages described herein, and each of such variations, modifications and improvements is deemed to be within the scope of the present invention. More generally, those skilled in the art would readily appreciate that all configurations described herein are meant to be exemplary and that actual configurations will depend upon specific applications for which the teachings of the present invention are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described. The present invention is directed to each individual feature, system, material and/or method described herein. In addition, any combination of two or more such features, systems, materials and/or methods, provided that such features, systems, materials and/or methods are not mutually inconsistent, is included within the scope of the present invention. In the claims (as well as in the specification above), all transitional phrases or phrases of inclusion, such as "comprising," "including," "carrying," "having," "containing," "composed of," "made of," "formed of," "involving" and the like shall be interpreted to be open-ended, i.e. to mean "including but not limited to" and, therefore, encompassing the items listed thereafter and equivalents thereof as well as additional items. Only the transitional phrases or phrases of inclusion "consisting of" and "consisting essentially of" are to be interpreted as closed or semi-closed phrases, respectively. In cases where the present specification and a document incorporated by reference include conflicting disclosure, the present specification shall control.

What is claimed:

1. A surgical instrument having a proximal end comprising a handle and a distal end located opposite the proximal end in an axial direction, the instrument comprising:
    a nozzle located at the distal end of the instrument that is shaped to form a liquid jet;
    a pressure lumen configured and positioned to convey a flow of liquid to the nozzle;
    an evacuation lumen located between the nozzle and the proximal end of the instrument in the axial direction, comprising a jet-receiving opening located opposite the nozzle to receive at least a portion of the liquid jet emitted from the nozzle, when the instrument is in operation, and which is configured and positioned to convey a flow of liquid away from the jet-receiving opening; and
    a curette tissue-excision component constructed and positioned at the distal end of the instrument to excise tissue during the surgical procedure, the curette tissue-excision component comprising a body portion located substantially opposite the jet-receiving opening and extending radially outward from a location defined by an axial center of the nozzle to a radial periphery, and a sharpened edge located at the radial periphery and extending circumferentially about the body portion in a direction substantially perpendicular to the axial center of the nozzle;
    wherein the nozzle is positioned between the jet-receiving opening and a portion of the curette tissue-excision component so that, during operation of the instrument, the liquid jet is directed so as to contact tissue excised by the curette tissue-excision component during a surgical procedure.

2. The surgical instrument of claim 1, wherein the curette tissue-excision component is configured to be non-rotating when the instrument is in operation.

3. The surgical instrument of claim 2, wherein the curette tissue-excision component is configured to remain stationary with respect to the position of the nozzle.

4. The surgical instrument of claim 1, wherein the body portion of the curette tissue-excision component comprises:
    a cup-shaped tissue receptacle configured and positioned to contain tissue excised by the curette tissue-excision component, wherein the nozzle is positioned, during operation of the instrument, to direct the liquid jet so that at least a portion of the liquid jet is contained within the receptacle.

5. The surgical instrument of claim 4, wherein at least a portion of a rim of the receptacle is sufficiently sharp to form a tissue-cutting blade comprising the sharpened edge of the body portion of the curette tissue-excision component.

6. The surgical instrument of claim 1, wherein the pressure lumen is configured to enable it to convey a high-pressure liquid at a pressure of at least 1,000 psig.

7. The surgical instrument of claim 6, wherein the pressure lumen is configured to enable it to convey a high-pressure liquid at a pressure of at least 2,000 psig.

8. The surgical instrument of claim 7, wherein the pressure lumen is configured to enable it to convey a high-pressure liquid at a pressure of at least 3,000 psig.

9. The surgical instrument of claim 8, wherein the pressure lumen is configured to enable it to convey a high-pressure liquid at a pressure of at least 5,000 psig.

10. The surgical instrument of claim 9, wherein the pressure lumen is configured to enable it to convey a high-pressure liquid at a pressure of at least 10,000 psig.

11. The surgical instrument of claim 10, wherein the pressure lumen is configured to enable it to convey a high-pressure liquid at a pressure of at least 15,000 psig.

12. The surgical instrument of claim 11, wherein the pressure lumen is configured to enable it to convey a high-pressure liquid at a pressure of at least 30,000 psig.

13. The surgical instrument of claim 1, wherein the evacuation lumen is shaped and positioned to enable it to remove from a surgical site at least a portion of the tissue excised by the tissue-excision component during operation.

14. The surgical instrument of claim 1, wherein the distal end of the surgical instrument is adapted to perform a surgical procedure on a patient, wherein the distal end of the surgical instrument has a shape and a size selected to facilitate insertion of the distal end into a region of the body of the patient defining a surgical site.

15. The surgical instrument of claim 14, wherein the region of the body of the patient defining the surgical site is the spine of the patient.

16. The surgical instrument of claim 1, wherein the evacuation lumen is shaped and positionable to enable evacuation of essentially all of the liquid comprising the liquid jet from the jet-receiving opening to the proximal end of the instrument, without the need for an external source of suction.

17. The surgical instrument of claim 1, wherein the proximal end is adapted to facilitate control of the instrument by an operator.

18. The surgical instrument of claim 17, wherein the handle comprises a grasping region shaped and positioned to facilitate gripping by a hand of an operator of the instrument.

19. The surgical instrument of claim 1, wherein a distance separating the jet-receiving opening of the evacuation lumen from the nozzle defines a length of the liquid jet emitted from the nozzle.

20. A kit comprising the surgical instrument of claim 1, in combination with instructions directing an operator to dispose of at least a portion of the instrument after a single use.

21. The kit of claim 20, wherein the instructions direct an operator to dispose of only a portion of the instrument after a single use and to reuse the remainder of the instrument.

22. The kit of claim 21, wherein the instructions direct an operator to dispose of at least one of the pressure lumen, the evacuation lumen, the nozzle, and the curette tissue-excision component.

23. The kit of claim 20, wherein the instructions direct an operator to dispose of the entire instrument after a single use.

24. The surgical instrument of claim 1, wherein the liquid jet emitted by the nozzle and directed so as to contact the tissue excised by the curette tissue-excision component is able to cut at least a portion of the excised tissue and drive at least a portion of the excised tissue into and at least partially through the evacuation lumen.

25. A surgical instrument having a proximal end comprising a handle and a distal end located opposite the proximal end, the surgical instrument comprising:

a non-liquid jet tissue-excision component constructed and positioned to excise tissue during a surgical procedure, wherein the non-liquid jet tissue-excision component comprises a cup-shaped tissue receptacle having a sharpened peripheral rim located at the distal end of the instrument, the sharpened peripheral rim extending circumferentially about the non-liquid jet tissue-excision component;

the tissue receptacle configured and positioned to capture excised tissue;

a nozzle located at the distal end of the instrument that is shaped to form a liquid jet and is positioned to direct the liquid jet towards the proximal end of the instrument so that at least a portion of the liquid jet is contained within the cup-shaped tissue receptacle, when the instrument is in operation; and a pressure lumen configured and positioned to convey a flow of liquid to the nozzle.

26. The surgical instrument of claim 25, wherein the surgical instrument comprises a curette.

27. The surgical instrument of claim 25, wherein at least an outlet portion of the nozzle is contained within the receptacle.

28. A surgical instrument having a proximal end comprising a handle and a distal end located opposite the proximal end, the surgical instrument comprising:

a curette device comprising:

a nozzle located at the distal end of the instrument that is shaped to form a liquid jet and positioned to direct the liquid jet towards the proximal end of the instrument;

a pressure lumen configured and positioned to convey a flow of liquid to the nozzle; and a curette tissue-excision component constructed and positioned at the distal end of the instrument to excise tissue during a surgical procedure, the curette tissue-excision component comprising an excision portion extending outward from a location defined by an axial center of the nozzle to a periphery, and a sharpened edge located at the periphery and extending circumferentially about the excision portion in a direction substantially perpendicular to the axial center of the nozzle.

29. The surgical instrument of claim 28, wherein the curette device further comprises:

an evacuation lumen comprising a jet-receiving opening locatable opposite the nozzle to receive at least a portion of the liquid jet emitted from the nozzle, when the instrument is in operation, and which is configured and positioned to convey a flow of liquid away from the jet-receiving opening.

30. The surgical instrument of claim 28, wherein the excision portion comprises:

a cup-shaped tissue receptacle configured and positioned to contain tissue excised by the curette tissue excision component, wherein the nozzle is positioned, during operation of the instrument, to direct the liquid jet so that at least a portion of the liquid jet is contained within the receptacle.

* * * * *